US010583084B2

(12) United States Patent
Peer

(10) Patent No.: US 10,583,084 B2
(45) Date of Patent: Mar. 10, 2020

(54) LIPOSOMAL FORMULATIONS FOR DELIVERY OF NUCLEIC ACIDS

(71) Applicant: RAMOT AT TEL-AVIV UNIVERSITY LTD., Tel Aviv (IL)

(72) Inventor: Dan Peer, Kiryat Ono (IL)

(73) Assignee: RAMOT AT TEL-AVIV UNIVERSITY LTD., Tel Aviv (IL)

(*) Notice: Subject to any disclaimer, the term of this patent is extended or adjusted under 35 U.S.C. 154(b) by 0 days.

(21) Appl. No.: 15/320,903

(22) PCT Filed: Jun. 25, 2015

(86) PCT No.: PCT/IL2015/050653
§ 371 (c)(1),
(2) Date: Dec. 21, 2016

(87) PCT Pub. No.: WO2015/198326
PCT Pub. Date: Dec. 30, 2015

(65) Prior Publication Data
US 2017/0128367 A1    May 11, 2017

Related U.S. Application Data

(60) Provisional application No. 62/017,276, filed on Jun. 26, 2014.

(51) Int. Cl.
*A61K 9/127* (2006.01)
*C12N 15/113* (2010.01)
*C12N 15/88* (2006.01)

(52) U.S. Cl.
CPC .......... *A61K 9/1272* (2013.01); *C12N 15/113* (2013.01); *C12N 15/88* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,235,871 A | 11/1980 | Papahadjopoulos et al. |
| 4,666,828 A | 5/1987 | Gusella |
| 4,683,202 A | 7/1987 | Mulls |
| 4,801,531 A | 1/1989 | Frossard |
| 4,879,219 A | 11/1989 | Wands et al. |
| 4,898,735 A | 2/1990 | Barenholz et al. |
| 4,902,512 A | 2/1990 | Ishigami et al. |
| 4,927,637 A | 5/1990 | Morano et al. |
| 5,011,771 A | 4/1991 | Bellet et al. |
| 5,143,713 A | 9/1992 | Phillips et al. |
| 5,192,659 A | 3/1993 | Simons |
| 5,272,057 A | 12/1993 | Smulson et al. |
| 5,281,521 A | 1/1994 | Trojanowski et al. |
| 5,401,511 A | 3/1995 | Margalit |
| 5,614,506 A | 3/1997 | Falk et al. |
| 5,624,839 A | 4/1997 | Yada et al. |
| 5,637,483 A | 6/1997 | Dranoff et al. |
| 5,639,738 A | 6/1997 | Falk et al. |
| 5,674,857 A | 10/1997 | Falk et al. |
| 5,733,892 A | 3/1998 | Sakurai et al. |
| 5,783,566 A | 7/1998 | Mislick |
| 5,792,753 A | 8/1998 | Falk et al. |
| 5,811,410 A | 9/1998 | Falk et al. |
| 5,817,642 A | 10/1998 | Falk et al. |
| 5,824,658 A | 10/1998 | Falk et al. |
| 5,827,834 A | 10/1998 | Falk et al. |
| 5,830,882 A | 11/1998 | Falk et al. |
| 5,834,444 A | 11/1998 | Falk et al. |

(Continued)

FOREIGN PATENT DOCUMENTS

JP    H09-511252 A    11/1997
JP    2003-528131 A    9/2003

(Continued)

OTHER PUBLICATIONS

European Application No. 13778205.8, Extended European Search Report, dated Jul. 29, 2015, 5 pages.
European Application No. 02761287.8, Supplementary European Search Report, dated Feb. 8, 2010, 3 pages.
International Search Report for International Application No. PCT/US2002/025178 dated Dec. 20, 2002, 1 page.
International Search Report and Written Opinion for International Application No. PCT/IL2010/000614 dated Jan. 21, 2011, 14 pages.
International Preliminary Report on Patentability for International Application No. PCT/IL2010/000614 dated Jan. 31, 2012, 9 pages.
International Search Report and Written Opinion for International Application No. PCT/IL2013/050238 dated Jun. 20, 2013, 10 pages.

(Continued)

*Primary Examiner* — Brian Gulledge
(74) *Attorney, Agent, or Firm* — Browdy and Neimark, PLLC

(57) ABSTRACT

There are provided liposomes, comprising cationic lipids, a membrane stabilizing lipid and at least one lipid conjugated to a polyethylene glycol (PEG) derivative, in particular PEG-amine, the liposomes are coated with a glycosaminoglycan, in particular, Hyaluronic Acid (HA), compositions comprising the same, methods for their preparation and uses thereof for the efficient delivery of nucleic acids, such as, si RNA molecules and for treating various conditions, such as cancer.

30 Claims, 13 Drawing Sheets
Specification includes a Sequence Listing.

(56) References Cited

U.S. PATENT DOCUMENTS

| | | |
|---|---|---|
| 5,847,002 A | 12/1998 | Willoughby et al. |
| 5,852,002 A | 12/1998 | Falk et al. |
| 5,910,489 A | 6/1999 | Falk et al. |
| 5,914,314 A | 6/1999 | Falk et al. |
| 5,914,322 A | 6/1999 | Falk et al. |
| 5,922,350 A | 7/1999 | Janoff et al. |
| 5,929,048 A | 7/1999 | Falk et al. |
| 5,932,560 A | 8/1999 | Falk et al. |
| 5,942,498 A | 8/1999 | Falk et al. |
| 5,962,433 A | 10/1999 | Falk et al. |
| 5,972,906 A | 10/1999 | Asculai et al. |
| 5,977,088 A | 11/1999 | Harper et al. |
| 5,985,850 A | 11/1999 | Falk et al. |
| 5,985,851 A | 11/1999 | Falk et al. |
| 5,990,095 A | 11/1999 | Falk et al. |
| 5,990,096 A | 11/1999 | Asculai et al. |
| 6,017,900 A | 1/2000 | Falk et al. |
| 6,022,866 A | 2/2000 | Falk et al. |
| 6,048,844 A | 4/2000 | Falk et al. |
| 6,069,135 A | 5/2000 | Falk et al. |
| 6,087,344 A | 7/2000 | Falk et al. |
| 6,103,704 A | 8/2000 | Falk et al. |
| 6,114,314 A | 9/2000 | Falk et al. |
| 6,136,793 A | 10/2000 | Falk et al. |
| 6,140,312 A | 10/2000 | Falk et al. |
| 6,147,059 A | 11/2000 | Falk et al. |
| 6,194,392 B1 | 2/2001 | Falk et al. |
| 6,207,178 B1 | 3/2001 | Westesen et al. |
| 6,218,373 B1 | 4/2001 | Falk et al. |
| 6,348,185 B1 | 2/2002 | Piwnica-Worms |
| 6,593,308 B2 | 7/2003 | Szoka |
| 6,986,902 B1 | 1/2006 | Chen et al. |
| 7,544,374 B2 | 6/2009 | Margalit et al. |
| 8,277,847 B2 | 10/2012 | Margalit et al. |
| 9,259,474 B2 | 2/2016 | Margalit et al. |
| 9,526,705 B2 | 12/2016 | Margalit et al. |
| 9,574,210 B2 | 2/2017 | Peer et al. |
| 2001/0008772 A1* | 7/2001 | Smith ............... A61K 9/1271 435/455 |
| 2001/0031740 A1 | 10/2001 | Unger et al. |
| 2001/0038851 A1 | 11/2001 | Allen et al. |
| 2001/0044528 A1 | 11/2001 | Innis et al. |
| 2002/0012998 A1 | 1/2002 | Gonda et al. |
| 2002/0061849 A1 | 5/2002 | Nielsen et al. |
| 2002/0131995 A1 | 9/2002 | Francis, Jr. |
| 2003/0175733 A1 | 9/2003 | Kirst et al. |
| 2004/0241248 A1 | 12/2004 | Margalit et al. |
| 2006/0019912 A1 | 1/2006 | Burkoth et al. |
| 2009/0155178 A1 | 6/2009 | Margalit et al. |
| 2009/0291131 A1 | 11/2009 | MacLachlan et al. |
| 2012/0129916 A1 | 5/2012 | Peer et al. |
| 2013/0095032 A1 | 4/2013 | Margalit et al. |
| 2013/0245107 A1* | 9/2013 | de Fougerolles ...... A61K 48/00 514/44 R |
| 2015/0140108 A1 | 5/2015 | Peer et al. |
| 2015/0216998 A1 | 8/2015 | Feinstein et al. |
| 2016/0113882 A1 | 4/2016 | Margalit et al. |
| 2016/0120804 A1* | 5/2016 | Barda-Saad ........... A61K 9/127 424/450 |

FOREIGN PATENT DOCUMENTS

| | | | |
|---|---|---|---|
| JP | 2011-507534 A | 3/2011 | |
| KR | 10-0806088 B1 | 2/2008 | |
| WO | WO 01/39815 * | 6/2001 | ............. A61K 9/127 |
| WO | WO 2001/039815 A2 | 6/2001 | |
| WO | WO 2003/015755 A1 | 2/2003 | |
| WO | WO 2007/127219 A2 | 11/2007 | |
| WO | WO 2007/127272 A2 | 11/2007 | |
| WO | WO 2009/020270 A1 | 2/2009 | |
| WO | WO 2009/026328 A2 | 2/2009 | |
| WO | 2011000107 A1 | 1/2011 | |
| WO | WO 2011/013130 A2 | 2/2011 | |
| WO | WO 2011/075656 A1 | 6/2011 | |
| WO | WO 2013/156989 A1 | 10/2013 | |
| WO | WO 2015/198326 A1 | 12/2015 | |

OTHER PUBLICATIONS

International Preliminary Report on Patentability for International Application No. PCT/IL2013/050238 dated Oct. 21, 2014, 8 pages.
International Search Report and Written Opinion for International Application No. PCT/IL2015/050653 dated Oct. 15, 2015, 13 pages.
International Preliminary Report on Patentability for International Application No. PCT/IL2015/050653 dated Dec. 27, 2016, 8 pages.
Aoki et al., "In vivo transfer efficiency of antisense oligonucleotides into the myocardium using HVJ-liposome method." Biochem Biophys Res Commun (1997); 231(3): 540-545.
Barkay, Zahava, et al. "Three-dimensional characterization of drug-encapsulating particles using STEM detector in FEG-SEM." Micron (2009); 40(4): 480-485.
Bhargava et al., "Long double-stranded RNA-mediated RNA interference as a tool to achieve site-specific silencing of hypothalamic neuropeptides." Brain Res Brain Res Protoc (2004); 13(2): 115-125.
Billy, et al., "Specific interference with gene expression induced by long, double-stranded RNA in mouse embryonal teratocarcinoma cell lines", PNAS (2001); 98(25): 14428-14433.
Britannica Online Encyclopedia, "liposome", downloaded Nov. 14, 2008 http://www.britannica.com/Ebchecked/topic/342910/liposome, 1 page.
Brummelkamp et al., "A system for stable expression of short interfering RNAs in mammalian cells." Science (2002); 296 (5567): 550-553.
Castanotto et al., "Functional siRNA expression from transfected Pcr products." RNA (2002); 8(11): 1454-1460.
Chekhonin, et al., "Immunoliposomal containers as systems of directed transport of minor interfering RNA into Schwann cells", Bulletin of Experimental Biology and Medicine (2008); 146(4): 451-454.
Choi et al., "Self-assembled hyaluronic acid nanoparticles for active tumor targeting." Biomaterials (2009); 31(1): 106-114.
Chono, et al., "An efficient and low immunostimulatory nanoparticle formulation for systemic siRNA delivery to the tumor", Journal of Controlled Release (2008); 131(1): 64-69.
Diallo et al., "Long endogenous dsRNAs can induce complete gene silencing in mammalian cells and primary cultures." Oligonucleotides (2003); 13(5): 381-392.
Dorland's Illustrated Medical Dictionary, "liposis", 30th edition, Saunders, PA, 2003, p. 1058, 3 pages.
Firth et al., "Studies on the use of antimitotic drugs entrapped within liposomes and of their action on a human glioma cell line," J Neurol Sci (1984); 63(2): 153-165.
Grishok et al., "Genes and mechanisms related to RNA interference regulate expression of the small temporal RNAs that control C.elegans developmental timing." Cell (2001); 106(1): 23-34.
Guo et al., "MicroRNA directs mRNA cleavage of the transcription factor NAC1 to downregulate auxin signals for *Arabidopsis* lateral root development." Plant Cell (2005); 17(5): 1376-1386.
Hammond et al., "Argonaute2, a link between genetic and biochemical analyses of RNAi." Science (2001); 293(5532): 1146-1150.
Han, et al., "Cationic derivatives of biocompatible hyaluronic acids for delivery of siRNA and antisense oligonucleotides", Journal of Drug Targeting (2009); 17(2): 123-132.
Herringson, et al., "Convenient targeting of stealth siRNA-lipoplexes to cells with chelator lipid-anchored molecules", Journal of Controlled Release (2009); 139(3): 229-238.
https://www.caymanchem.com/app/template/Product.vm/catalog/15084, retrieved from the internet on Apr. 19, 2015, 2 pages.
Huang, Chin-Yi, et al. "Lipitoids—novel cationic lipids for cellular delivery of plasmid DNA in vitro." Chemistry & Biology (1998); 5(6): 345-354.
Hutvágner and Zamore, "A microRNA in a multiple-turnover RNAi enzyme complex." Science (2002); 297(5589): 2056-2060.

(56) References Cited

OTHER PUBLICATIONS

Hutvágner et al., "A cellular function for the RNA-interference enzyme Dicer in the maturation of the let-7 small temporal RNA." Science (2001); 293(5531): 834-838.
Jiang, et al., "Hyaluronic acid-polyethyleneimine conjugate for target specific intracellular delivery of siRNA", Biopolymers (2008); 89(7): 635-642.
Jiang, et al., "Target Specific Intracellular Delivery of siRNA/PEI-HA Complex by Receptor Mediated Endocytosis", Molecular Pharmaceutics (2009); 6(3): 727-737.
Ketting et al., "Dicer functions in RNA interference and in synthesis of small RNA involved in developmental timing in C.elegans." Genes Dev (2001); 15(20): 2654-2659.
Kronenwett et al., "Oligodeoxyribonucleotide uptake in primary human hematopoietic cells is enhanced by cationic lipids and depends on the hematopoietic cell subset." Blood (1998); 91(3): 852-862.
Kundu et al., "Stability of lyophilized siRNA nanosome formulations." Int J Pharm (2012); 423(2): 525-534.
Landesman-Milo, D and Peer, D., "Toxicity profiling of several common RNAi-based nanomedicines: a comparative study." Drug Deliv. and Transl.Res. (2013); 4(1): 96-103 (published online May 29, 2013) DOI 10.1007/s13346-013-0158-7).
Lasic, Danilo D. "Liposomes", Liposomes in gene delivery, CRC press, 1997, Ch. 6, pp. 67-68.
Lavigne and Thierry, "Enhanced antisense inhibition of human immunodeficiency virus type 1 in cell cultures by DLS delivery system." Biochem Biophys Res Commun (1997); 237(3): 566-571.
Lee et al., "Target-specific intracellular delivery of siRNA using degradable hyaluronic acid nanogels." J Control Release (2007); 119(2): 245-252.
Lee et al., "The C.elegans heterochronic gene lin-4 encodes small RNAs with antisense complementarity to lin-14." Cell (1993); 75(5): 843-854.
Luft, "Making sense out of antisense oligodeoxynucleotide delivery: getting there is half the fun." J Mol Med (Berl) (1998); 76(2): 75-76.
Matveeva et al., "Prediction of antisense oligonucleotide efficacy by in vitro methods." Nat Biotechnol (1998); 16(13): 1374-1375.
Manjunath and Dykxhoorn, "Advances in synthetic siRNA delivery." Discovery Medicine (2010); 9(48): 418-430.
Merriam Webster Online Dictionary, "liposome", downloaded Nov. 14, 2008 http://www.merriam-webster.com/dictionary/liposome, 1 page.
Monsigny et al., "Sugar-lectin interactions: how does wheat-germ agglutinin bind sialoglycoconjugates?" Eur J Biochem (1980); 104(1): 147-153.
Mourelatos et al., "miRNPs: a novel class of ribonucleoproteins containing numerous microRNAs." Genes Dev (2002); 16(6): 720-728.
Nakajima, et al., "Mechanism of amide formation by carbodiimide for bioconjugation in aqueous media", Bioconjugate Chem. (1995); 6(1): 123-130.
O'Reilly, et al., "Endostatin: an endogenous inhibitor of angiogenesis and tumor growth", Cell (1997); 2(88): 277-285.
Paddison et al., "Stable suppression of gene expression by RNAi in mammalian cells." Proc Nall Acad Sci U S A (2002); 9(3): 1443-1448.
Parizotto et al., "In vivo investigation of the transcription, processing, endonucleolytic activity, and functional elevance of the spatial distribution of a plant miRNA." Genes Dev (2004); 18(18): 2237-2242 and erratum.
Peer, "Induction of therapeutic gene silencing in leukocyte-implicated diseases by targeted and stabilized nanoparticles: A mini-review." J Controlled Release (2010); 148(1): 63-68.
Peer, et al., "Systemic leukocyte-directed siRNA delivery revealing cyclin D1 as an anti-Inflammation target." Science (2008); 319(5863): 627-630.
Peer, et al., "Hyaluronan is a key component in cryoprotection and formulation of targeted unilamellar liposomes", Biochimica et Biophysica Acta (2003); 1612(1): 76-82.
Peer, et al., "Selective gene silencing in activated leukocytes by targeting siRNAs to the integrin lymphocyte function-associated antigen-1", PNAS (2007); 104(10): 4095-4100.
Peer, et al., "Physicochemical evaluation of a stability-driven approach to drug entrapment in regular and in surface-modified liposomes", Archives of Biochemistry and Biophysics (2000); 383(2): 185-190.
Peer, D and Shimaoka, M. "Systemic siRNA delivery to leukocyte-implicated diseases." Cell Cycle (2009); 8(6): 853-859.
Pierce 1994 Catalog, 4 pages.
Rajur et al., Covalent protein—0ligonucleotide conjugates for efficient delivery of antisense molecules. Bioconjug Chem (1997); 8(6): 935-940.
Rivkin, Ilia, et al. "Paclitaxel-clusters coated with hyaluronan as selective tumor-targeted nanovectors." Biomaterials (2010); 31(27): 7106-7114.
Romberg, Birgit, et al. "Enzyme-induced shedding of a poly (amino acid)-coating triggers contents release from dioleoyl phosphatidylethanolamine liposomes." International Journal of Pharmaceutics (2008); 355(1): 108-113.
Rose et al., "Functional polarity is introduced by Dicer processing of short substrate RNAs." Nucleic Acids Res (2005); 33(13): 4140-4156.
Ruozi, Barbara, et al. "Immunoliposomal systems targeting primary effusion lymphoma: in vitro study." Nanomedicine (2010); 5(7): 1051-1064.
Saul, Justin M., et al. "Controlled targeting of liposomal doxorubicin via the folate receptor in vitro." Journal of Controlled Release (2003); 92(1): 49-67.
Shinagawa and Ishii, "Generation of Ski-knockdown mice by expressing a long double-strand RNA from an RNA polymerase II promoter." Genes Dev (2003); 17(11): 1340-1345.
Strat et al., "Specific and nontoxic silencing in mammalian cells with expressed long dsRNAs." Nucleic Acids Res (2006); 34(13): 3803-3810.
Surace, et al., "Lipoplexes targeting the CD44 hyaluronic acid receptor for efficient transfection of breast cancer cells", Molecular Pharmaceutics (2009); 6(4): 1062-1073.
Taetz et al., "Hyaluronic acid-modified DOTAP/DOPE liposomes for the targeted delivery of anti-telomerase siRNA to CD44-expressing lung cancer cells." Oligonucleotides (2009); 19(2): 103-116.
Tam, Yuen Yi C., et al. "Advances in lipid nanoparticles for siRNA delivery." Pharmaceutics (2013); 5(3): 498-507.
Thermo Scientific Crosslinking Technical Handbook, Jan. 1, 2012, XP55272448; Retrieved from the Internet: Url: hllps://tools.thermofisher.com/contenl/sfs/brochures/1602163-Crosslinking-Reagents-Handbook.pdf; 56 pages.
Torchilin, Vladimir P. "Recent advances with liposomes as pharmaceutical carriers." Nature Reviews Drug Discovery (2005); 4(2): 145-160.
Tran et al., "Control of specific gene expression in mammalian cells by co-expression of long complementary RNAs." FEBS (2004); Lett 573(1-3): 127-134.
Tuschl, "RNA interference and small interfering RNAs." Chembiochem (2001); 2(4): 239-245.
Walton et al., "Prediction of antisense oligonucleotide binding affinity to a structured RNA target." Biotechnol Bioeng (1999); 65(1): 1-9.
Weinstein and Peer, "RNAi nanomedicines: challenges and opportunities within the immune system." Nanotechnology (2010); 21(23): 1-13.
Wightman et al., "Posttranscriptional regulation of the heterochronic gene lin-14 by lin-4 mediates temporal pattern formation in C. elegans." Cell (1993); 75(5): 855-862.
Williams and Rubin, ARGONAUTE1 is required for efficient RNA interference in *Drosophila* embryos. Proc Natl Acad Sci USA (2002); 99(10): 6889-6894.

(56) References Cited

OTHER PUBLICATIONS

Yagi et al., "Interferon-beta endogenously produced by intratumoral injection of cationic liposome-encapsulated gene: cytocidal effect on glioma transplanted into nude mouse brain," Biochem Mol Biol Int (1994); 32(1): 167-171.

Yen et al., "CD44 Mediated Nonviral Gene Delivery into Human Embryonic Stem Cells via Hyaluronic-Acid-Coated Nanoparticles." ACS Biomater Sci Eng (2016); 2(3): 326-335.

Yu, et al., "let-7 regulates self renewal and tumorigenicity of breast cancer cells", Cell (2007); 131(6): 1109-1123.

Zeng et al., "Both natural and designed micro RNAs can inhibit the expression of cognate mRNAs when expressed in human cells." Mol Cell (2002); 9(6): 1327-1333.

Arpicco et al., (2013) Lipid-Based Nanovectors for Targeting of CD44-Overexpressing Tumor Cells. J Drug Deliv 2013: 860780; 9 pages.

Cohen et al., (2014) Modulation of Drug Resistance in Ovarian Adenocarcinoma Using Chemotherapy Entrapped in Hyaluronan-Grafted Nanoparticle Clusters. ACS Nano 8(3): 2183-2195 and supportive info.

Cohen et al., (2015) Localized RNAi therapeutics of chemoresistant grade IV glioma using hyaluronan-grafted lipid-bpased nanoparticles. ACS Nano 9(2): 1581-91 and supportive info.

Karpel-Massler et al., (2013) Combined inhibition of HER1/EGFR and RAC1 results in a synergistic antiproliferative effect on established and primary cultured human glioblastoma cells. Mol Cancer Ther 12(9): 1783-95.

Erogbogbo et al., (2013) Bioengineering silicon quantum dot theranostics using a network analysis of metabolomic and proteomic data in cardiac ischemia. Theranostics 3(9): 719-28.

Jayaraman et al., (2012) Maximizing the potency of siRNA lipid nanoparticles for hepatic gene silencing in vivo. Angew Chem Int Ed Engl 51(34): 8529-33.

Landesman-Milo et al., (2013) Hyaluronan grafted lipid-based nanoparticles as RNAi carriers for cancer cells. Cancer Lett 334(2): 221-7.

Liu et al., (2011) A lipid nanoparticle system improves siRNA efficacy in RPE cells and a laser-induced murine CNV model. Invest Ophthalmol Vis Sci 52(7): 4789-94.

Mizrahy et al., (2011) Hyaluronan-coated nanoparticles: the influence of the molecular weight on CD44-hyaluronan interactions and on the immune response. J Control Release 156(2): 231-8.

Ramishetti et al., (2015) Systemic Gene Silencing in Primary T Lymphocytes Using Targeted Lipid Nanoparticles. ACS Nano 9(7): 6706-16 and supportive info.

Sakurai et al., (2014) Improvement of doxorubicin efficacy using liposomal anti-polo-like kinase 1 siRNA in human renal cell carcinomas. Mol Pharm 11(8): 2713-9.

Schroeder et al., (2010) Lipid-based nanotherapeutics for siRNA delivery. J Intern Med 267(1): 9-21.

Shim et al., (2013) Application of cationic liposomes for delivery of nucleic acids. Asian Journal of Pharmaceutical Sciences 8(2): 72-80.

Shulman and Alon (2009) Chapter 14 Real-Time in Vitro Assays for Studying the Role of Chemokines in Lymphocyte Transendothelial Migration Under Physiological Flow Conditions. Methods in Enzymology 461: 311-332.

Singh (2013) Nanomaterials as Non-viral siRNA Delivery Agents for Cancer Therapy. Bioimpacts 3(2): 53-65.

Weinstein et al., (2012) RNA inhibition highlights cyclin D1 as a potential therapeutic target for mantle cell lymphoma. PLoS One 7(8): e43343; 5 pages.

Yao et al., (2012) Targeted delivery of PLK1-siRNA by ScFv suppresses Her2+ breast cancer growth and metastasis. Sci Transl Med 4(130): 130ra48; 11 pages.

Yi et al., (2014) Combined delivery of BCNU and VEGF siRNA using amphiphilic peptides for glioblastoma. J Drug Target 22(2): 156-64.

Eliaz and Szoka (2001) Liposome-encapsulated doxorubicin targeted to CD44: a strategy to kill CD44-overexpressing tumor cells. Cancer Res 61(6): 2592-2601.

\* cited by examiner

| Patient ID | CD 44 expression | Pathology |
|---|---|---|
| 9558/10 | +++ | GBM |
| 3970/10 | + | GBM |
| 10105/10 | +++ | GBM |
| 15081/10 | +++ | GBM |
| 14784/10 | +++ | GBM |
| 19037/10 | ++ | GBM |
| 20688/10 | ++/+++ | GBM |
| 22712/10 | +++ | GBM |

Fig. 7A
Fig. 7B
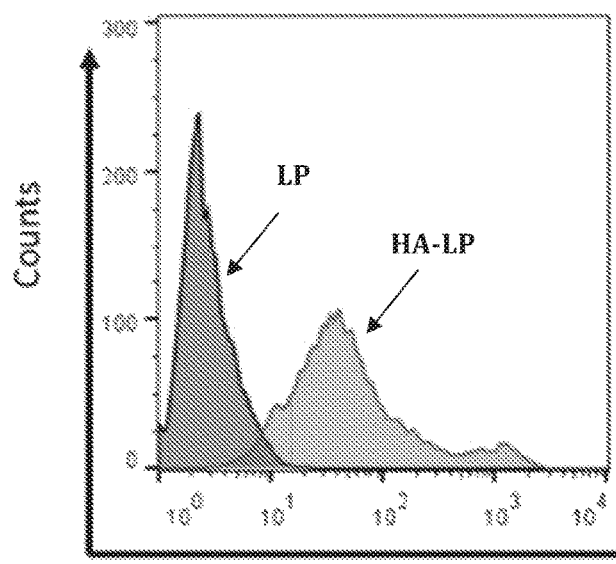
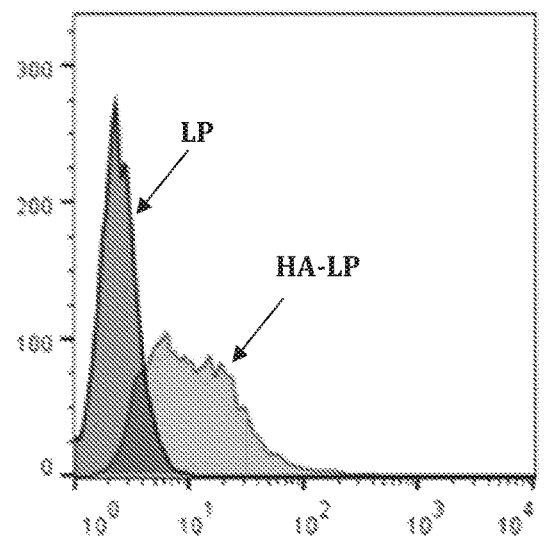
Fig. 8
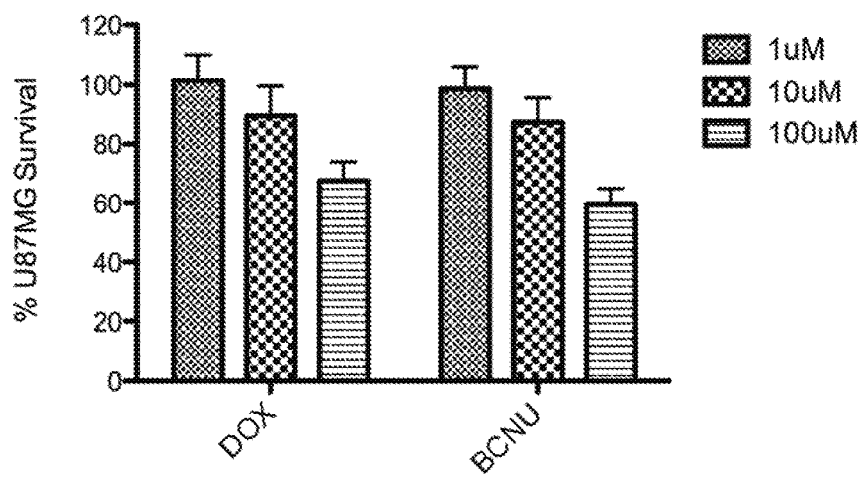

LIPOSOMAL FORMULATIONS FOR DELIVERY OF NUCLEIC ACIDS

FIELD OF THE INVENTION

The present invention relates to liposomes comprising cationic lipids, compositions comprising the same, methods for their preparation and uses thereof for the efficient delivery of nucleic acids, such as, siRNA molecules and for treating various conditions, such as, cancer.

BACKGROUND OF THE INVENTION

Efficient delivery of a nucleic acid to a desired target site has been the focus of many intense studies. Once introduced to the target site, the nucleic acid may exert, directly or indirectly, a biological effect in the target site. In some instances, the delivery of the nucleic acid may take use of carriers that are designed to deliver the nucleic acid to the target site. Exemplary nucleic acids that may be delivered to a target site include deoxyribonucleotides nucleic acid (DNA) and ribonucleotides nucleic acids (RNA), such as, for example, siRNA, miRNA, shRNA, Antisense RNA (AS-RNA), and the like.

For in-vitro or ex-vivo delivery of siRNA to cells, conventional transfection methods are generally used. In-vivo delivery of siRNA can be classified into two groups: localized or systemic. Whereas cellular and local delivery deal with the need for internalization, release, and accumulation of the siRNAs in the cell cytoplasm, systemic delivery in an entire animal enforces additional hurdles such as, for example, the siRNAs interaction with blood components, entrapment within capillaries, uptake by the reticuloendothelial cells, degradation by RNases, anatomical barriers (such as the liver, spleen and filtration by the kidneys), immune stimulation, extravasation from blood vessels to target tissues, permeation within the tissue, and the like.

Various methods and carriers have been suggested for systemic delivery of siRNA molecules. The methods and carriers include passive delivery of the siRNA or targeted delivery of the siRNA. Exemplary carriers described in the art include: Stable nucleic acid-lipid particles (SNALP), neutral liposomes, lipidated glycosaminoglycan particles (Gagomers), lipidoid containing liposomes, Pegylated liposomes, atelocollagen, cholesterol-siRNA, dynamic polyconjugates, PEI nanoplexes, antibody-protamine fusion proteins, aptamer-siRNAs, targeted cationic liposomes and cyclodextrin containing polycation (CDP). (reviewed by Weinstein and Peer (2010), Schroder et al., (2010) and Shim et al. (2013)). For example, a publication by Liu et al. is directed to A Lipid Nanoparticle System Improves siRNA Efficacy in RPE Cells and a Laser-Induced Murine CNV Model. For example, a publication by Shim et al., is directed to application of cationic liposomes for delivery of nucleic acids. For example, PCT patent application publication no. WO 2011/075656 is directed to methods and compositions for delivery of nucleic acids.

Some of the nucleic acid carriers described in the art make use of hyaluronic acid that may be used as component of the particle and/or as a targeting moiety. For example: A publication by Taetz et al., is directed to Hyaluronic acid modified DOTAP/DOPE liposomes for the targeted delivery of anti-telomerase siRNA to CD44 Expressing Lung cancer cells. A publication by Lee. et al. is directed to target specific intracellular delivery of siRNA using degradable hyaluronic acid nanogels. A publication by Choi et al., is directed to self assembled hyaluronic acid nanoparticles for active tumor targeting. A publication by Peer et al., is directed to Systemic Leukocyte-Directed siRNA Delivery Revealing Cyclin D1 as an Anti-Inflammatory Target. For example, a publication by Arpicco et al., is directed to Lipid-Based Nanovectors for Targeting of CD44-Overexpressing Tumor Cells. For example, US Patent application no. US 2002/0012998 is directed to cationic liposomes. For example, PCT patent application publication no. WO 2011/013130 is directed to cell targeting nanoparticles comprising polynucleotide agents and uses thereof. Additionally, U.S. Pat. No. 7,544,374 is directed to lipidated glycosaminoglycan particles and their use in drug and gene delivery for diagnosis and therapy. A publication by Cohen et. al. (2015) is directed to Localized RNAi Therapeutics of Chemo-Resistant Grade IV Glioma using Hyaluronan-Grafted Lipid-Based Nanoparticles.

Nevertheless, the carriers described in the art, including carriers making use of hyaluronic acid do not address all the hurdles associated with a successful delivery of nucleic acids, such as, siRNA to a target cell, and in particular, in-vivo delivery.

There is thus a need in the art for compositions for the efficient and specific delivery of nucleic siRNA into a desired target site, wherein the carrier compositions are stable, have a long shelf life, biodegradable, amenable to industrial production processes, have high encapsulating capacity, non toxic, avoid induction of immune responses, provide enhanced protection (stability and integrity) to the siRNA encapsulated therein and are able to efficiently deliver in-vitro and in-vivo, the siRNA to its target site, such that the siRNA is able to efficiently exert a desired effect.

SUMMARY OF THE INVENTION

The present invention provides liposomes that include a plurality of lipids comprising cationic lipid(s), membranes stabilizing lipids, and at least one lipid covalently conjugated to a poly-ethylene glycol (PEG) derivative coated with a glycosaminoglycan that is bound to the PEG derivative. According to some embodiments, the PEG derivative is a PEG-amine that bears an amino group that can bind to the carboxylic groups of the glycosaminoglycan. In some embodiments, the liposomes further comprise nucleic acid molecules. Such liposomes are useful as an effective and efficient in-vivo and in-vitro delivery system of nucleic acid molecules, such as, for example, siRNA molecules.

The present invention is based at least in part on the surprising and unexpected finding that inclusion of PEG derivatives, and in particular, PEG-amine derivatives, stabilizes the structure of the disclosed cationic liposomes and further serves as an anchor for the attachment of the glycosaminoglycan molecules that coat the surface of the liposomes. According to some embodiments, the glycosaminoglycan is hyaluronic acid (HA) of various molecular weights. As further disclosed herein for the first time, the cationic liposomes, which include the PEG derivatives are surprisingly and unexpectedly more stable as compared to similar lipid based compositions, which do not include PEG-amine or other PEG-derivatives. Moreover, as exemplified hereinbelow, the liposomes of the present disclosure advantageously have a relatively small polydispersion index (PDI). Furthermore, as exemplified hereinbelow, the liposomes of the present disclosure advantageously can be more easily controlled, such that the size of the glycosaminoglycan coated particles is not greater than about 300 nm-500 nm in diameter, which renders them advantageous for both in-vitro and in-vivo delivery of nucleic acid molecules. Additionally, the methods of preparation of the particles are advantageously commercially applicable, robust, cost effective and are amenable to scale up.

According to one aspect the present invention provides a cationic liposome for delivery of a nucleic acid, comprising: a) a lipid membrane comprising a cationic lipid, a membrane stabilizing lipid and PEG-amine conjugated to a lipid; b) a nucleic acid encapsulated within the liposome; and c) a glycosaminoglycan bound to the PEG amine derivative and coating the external surface of the liposome.

According to another aspect the present invention provides a composition for delivery of a nucleic acid, comprising a plurality of liposomes, the liposomes comprising a plurality of lipids comprising cationic lipid, membranes stabilizing lipid and at least one lipid conjugated to a polyethylene glycol (PEG) derivative, wherein the liposomes are coated with glycosaminoglycan molecules, bound to the PEG derivative; and a nucleic acid encapsulated within the liposomes.

According to some embodiments, there is provided a composition comprising liposomes comprising a plurality of lipids comprising cationic lipid, membranes stabilizing lipids and at least one lipid conjugated to a polyethylene glycol (PEG) derivative; and a nucleic acid encapsulated within the liposomes, wherein the liposomes are coated with glycosaminoglycan molecules (such as HA), bound to the PEG derivative.

In some embodiments, the liposomes (the lipid phase/ membranes thereof) may further comprise one or more additional lipids, selected from, but not limited to: ionized lipids and phosphatidylethanolamines.

In some embodiments, additional PEG derivatives (other than PEG-Amine) may be included in the lipids phase of the liposomes. The additional PEG derivatives may be modified with moieties that improve their binding or other properties. In some embodiments, the additional PEG derivatives may be conjugated to one or more additional molecules, such as, lipids.

In some embodiments, the PEG-Amine conjugated to the lipid may be selected from, but not limited to: 1,2-distearoyl-sn-glycero-3-phosphoethanolamine-N-[amino(polyethylene glycol)-2000] (DSPE-PEG-Amine); 1,2-Dilauroyl-sn-glycero-3-phosphoethanolamine (DLPE)-conjugated to PEG-Amine; 1,2-di-(9Z-octadecenoyl)-sn-glycero-3-phosphoethanolamine DOPE-conjugated to PEG-Amine, and 1,2-dipalmitoyl-sn-glycero-3-phosphoethanolamine (DPPE)-conjugated to PEG-Amine, and the like or combinations thereof. Each possibility is a separate embodiment. In some embodiments, the PEG-Amine provides a primary amine to which additional molecules may be attached or reacted. In some embodiments, the PEG-Amine is conjugated to a lipid. In some embodiments, the PEG-amine is conjugated to a phospholipid.

In some embodiments, the additional PEG derivative may be selected from, but not limited to: PEG-DMG (with the option to include an amine group at the end of the molecule), PEG-cDMA, 3-N-(-methoxy poly(ethylene glycol)2000) carbamoyl-1,2-dimyristyloxy-propylamine; PEG-cDSA, 3-N-(-methoxy poly(ethylene glycol)2000)carbamoyl-1,2-distearyloxy-propylamine, and the like or combinations thereof. Each possibility is a separate embodiment.

In some embodiments, the cationic lipids may be synthetic cationic lipids. In some embodiments, the cationic lipids may be selected from, but not limited to: DLinDMA, DLin-MC3-DMA and DLin-KC2-DMA; monocationic lipid N-[1-(2,3-Dioleoyloxy)]-N,N,N-trimethylammonium propane (DOTAP), BCAT O-(2R-1,2-di-O-(1'Z, 9'Z-octadecadienyl)-glycerol)-3-N-(bis-2-aminoethyl)-carbamate, BGSC (Bis-guanidinium-spermidine-cholesterol), BGTC (Bis-guanidinium-tren-cholesterol), CDAN (N'-cholesteryl oxycarbony 1-3,7-diazanonane-1,9-diamine), CHDTAEA (Cholesteryl hemidithiodiglycolyl tris(amino(ethyl)amine), DCAT (O-(1,2-di-O-(9'Z-octadecanyl)-glycerol)-3-N-(bis-2-aminoethyl)-carbamate), DC-Chol (3β [N—(N',N'-dimethylaminoethane)-carbamoyl] cholesterol), DLKD (O,O'-Dilauryl N-lysylaspartate), DMKD (O,O'-Dimyristyl N-lysylaspartate), DOG (Diolcylglycerol, DOGS (Diocta-decylamidoglycylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), DOTAP (1,2-Uiolcoyl-3-trimethyl ammoniopropane), DOTMA (N'[1-(2,3-Dioleyloxy)propyl]-N,N,N-trimethylammonium chloride), DPPES (Di-palmitoyl phosphatidyl ethanolamidosperminc), DDAB and DODAP. Each possibility is a separate embodiment.

In some exemplary embodiments, the cationic lipid has a pKa in the range of about 6.5-7. In some embodiments, the cationic lipid is selected from, but not limited to: DLinDMA, (with lipid pKa of 6.8), DLin-MC3-DMA (with lipid pKa of about 6.44) and DLin-KC2-DMA (with lipid pKa of about 6.7), or combinations thereof.

In some embodiments, the membrane stabilizing lipid may be selected from, but not limited to: cholesterol, phospholipids, cephalins, sphingolipids (sphingomyelins and glycosphingolipids), glycoglycerolipids, and the like, or combinations thereof. Each possibility is a separate embodiment.

In some embodiments, the phospholipids may be selected from, but not limited to: phosphatidylcholine (PC), phosphatidylethanolamine, phosphatidylinositol, phosphatidylserine, phosphatidylglycerol, diphosphatidylglycerols or any derivatives or combinations thereof. Each possibility is a separate embodiment.

In some embodiments, the Phosphatidylethanolamines may be selected from, but not limited to: 1,2-dilauroyl-L-phosphatidyl-ethanolamine (DLPE), 1,2-Dioleoyl-sn-glycero-3-phosphoethanolamine (DOPE) 1,2-Diphytanoyl-sn-glycero-3-phosphoethanolamine (DPhPE) 1,3-Dipalmitoyl-sn-glycero-2-phosphoethanolamine (1,3-DPPE) 1-Palmitoyl-3-oleoyl-sn-glycero-2-phosphoethanolamine (1,3-POPE) Biotin-Phosphatidylethanolamine, 1,2-Dimyristoyl-sn-glycero-3-phosphoethanolamine (DMPE), Dipalmitoylphosphatidylethanolamine (DPPE)) and 1,2-Distearoyl-sn-glycero-3-phosphoethanolamine (DSPE). Each possibility is a separate embodiment.

In some embodiments, the Phosphatidylethanolamines may be conjugated to a PEG-amine derivative.

According to further embodiments, the glycosaminoglycan may be selected from, but not limited to: hyaluronic acid (HA), Chondroitin sulfate, Dermatan sulfate, Keratan sulfate, Heparin, Heparan sulfate, as well as fragments, salts, and mixtures thereof. In some embodiments, the hyaluronic acid may be selected from, but not limited to: high molecular weight hyaluronic acid, low molecular weight hyaluronic acid, or combinations thereof, at various chain lengths. In some embodiments, the hyaluronic acid may have a molecular weight of about 1 kDa to 5000 kDa. In some embodiments, the hyaluronic acid may have a molecular weight of about 1 kDa to 1000 kDa. In some embodiments, the hyaluronic acid may have a molecular weight of about 5 kDa to 850 kDa. In some embodiments, the hyaluronic acid may have a molecular weight of about 5 kDa to 10 kDa. In some embodiments, the hyaluronic acid may have a molecular weight of about 5 kDa. In some embodiments, the hyaluronic acid may have a molecular weight of about 7 kDa. In some embodiments, the hyaluronic acid may have a molecular weight of about 600 kDa to 1000 kDa. Each possibility is a separate embodiment.

According to some embodiments, the liposomes of the present invention (i.e., including the outer glycosaminoglycan coating and a nucleic acid encapsulated within) have a particle size of about 20-500 nm in diameter.

In some embodiments, the nucleic acid encapsulated/entrapped/carried within the liposome may be selected from DNA, RNA, modified forms thereof, and combinations thereof. In some embodiments, the RNA may be selected from siRNA, miRNA, antisense RNA, mRNA, modified mRNA or combinations thereof.

In further embodiments, the liposomes may further include a targeting moiety.

In additional embodiments, the liposomes are capable of delivering nucleic acid encapsulated within the lipid structure (lipid phase/membranes) to a target site. The target site may be selected from a cell, a tissue, an organ, and a microorganism. In some embodiments, the target site is recognized by the glycosaminoglycan coating the particles. In some exemplary embodiments, the target site comprises a CD44 receptor and the glycosaminoglycan is HA.

According to some embodiments, there is provided a pharmaceutical composition comprising a plurality of liposomes encapsulating/carrying a nucleic acid, in a dosage form suitable for administration via a route selected from oral, parenteral and topical.

According to additional embodiments, the liposomes may be in the form of freeze dried particles or lyophilized particles.

According to exemplary embodiments, the liposomes of the present invention may comprise: synthetic cationic lipids, selected from, DLinDMA, DLin-MC3-DMA and DLin-KC2-DMA; phospholipid such as, phosphatidylcholine (PC) (for example, DSPC); a membrane stabilizing lipid, such as, cholesterol; a polyethylene glycol-amine derivative conjugated to a lipid (such as, PE); an additional PEG derivative conjugated to a lipid (such as DMG-PEG); a glycosaminoglycan, such as, Hyaluronic acid, conjugated to the primary amine derived from the PEG-amine and a nucleic acid encapsulated within the liposome.

According to some embodiments, there is provided a method for treatment of cancer in a subject in need thereof, the method comprising administering to the subject a composition comprising the cationic liposomes of the present disclosure, which include or encapsulate a nucleic acid, or a pharmaceutical composition comprising the same. In some embodiments, the nucleic acid may be selected from DNA, RNA, modified forms thereof, and combinations thereof. In some embodiments, the RNA may be selected from siRNA, miRNA, shRNA, antisense RNA, mRNA, modified mRNA or combinations thereof. In some embodiments, the cancer is glioma. In some embodiments, the glioma is glioblastoma multiforme (GBM).

In some embodiments, there is provided composition comprising the cationic liposomes of the present disclosure, which include or encapsulate a nucleic acid, or a pharmaceutical composition comprising the same for use is treating cancer, such as, Glioma.

According to some embodiments, there is provided a method for the preparation of a glycosaminoglycan coated liposome for delivery of a nucleic acid, the method comprising the steps of:
  a) forming a lipid phase comprising the step of mixing cationic lipid, membrane stabilizing lipid and PEG-Amine conjugated to a phospholipid, in an organic solvent at a desired ratio and forming a lipid mixture,
  b) generating the liposome by the step of:
    introducing a nucleic acid in an aqueous solution into the lipid mixture of step a); and
  c) adding an activated glycosaminoglycan to the mixture.

According to some embodiments, there is provided a method for the preparation of a glycosaminoglycan coated liposome for delivery of a nucleic acid, the method comprising the steps of:
  a) forming a lipid phase comprising the steps of:
    i) mixing cationic lipids, membrane stabilizing lipid and PEG-Amine conjugated to a lipid, in an organic solvent at a desired ratio and forming a lipid mixture,
    ii) suspending the lipid mixture in a buffer to generate multilamellar vesicles;
  b) generating the liposome by the steps of:
    i) incubating the lipid phase of step a) with the nucleic acid; and
    ii) adding an activated glycosaminoglycan to the mixture.

According to certain embodiments the organic solvent is selected from ethanol, chloroform, methanol, and the like.

According to certain embodiments, the buffer is an aqueous buffer. In some embodiments, the buffer is an acidic aqueous buffer. In some exemplary embodiments, the buffer is acetate buffer. In some embodiments, the buffer is MES Buffer, pH. 5.5

In some embodiments, the nucleic acid, in an acidic buffer may be added to the one or more lipids, prior to formation of multilamellar vesicles.

According to some embodiments, there is provided a method for the preparation of a glycosaminoglycan coated liposome for delivery of a nucleic acid, the method comprising the steps of:
  a) forming a lipid phase comprising the steps of:
    i) mixing cationic lipids, membrane stabilizing lipid and PEG-Amine conjugated to a lipid, in an organic solvent at a desired ratio and forming a lipid mixture,
    ii) suspending the lipid mixture in a buffer to generate multilamellar vesicles;
  b) generating the liposome by the steps of:
    i) incubating the lipid phase of step a) with the nucleic acid; and
  ii) adding an activated glycosaminoglycan to the mixture.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in the figures. Dimensions of components and features shown in the figures are generally chosen for convenience and clarity of presentation and are not necessarily shown to scale. The figures are listed below.

FIGS. 2 B-E: pictograms of surface characterization of exemplary liposomes (comprised of: DLinMC3-DMA/DSPC/Chol/DMG-PEG/DCPE-PEG-Amine (mol/mol 50:10:38:18:1.5:0.5) alone (FIGS. 2B and 2D) or conjugated to HA (5 KDa MW) (FIGS. 2C and 2E).

Fig. 6A—Representative FACS analysis of CD44 expression in GBM cell lines. An anti pan-CD44 mAb was used to stain three different GBM cell lines: T98G, U87MG and U251. ("−" no stain; "Ctrl− isotype control mAb; "CD44"—anti pan-CD44 mAb (clone IM7); FIG. 6B. CD44 expression in primary glioma samples excreted from patients using immunohistochemistry analysis as detailed. Analysis score was based on CD44 scattering within the tumor site. This staining is semiquantitatively scored; +(positive), ++(strongly positive), or +++(very strongly positive).

FIGS. 7A-B: liposomal particles comprising HA bind specifically to glioma cells. Liposomal particles (comprising or not comprising HA) which entrap/encapsulate a Cy5-siRNA as a control marker were used and analyzed for Cy5 presence in GBM (U87MG) cells by FACS analysis. FIG. 7A shows Representative FACS histograms of Particles comprising HA (HA-LP, which specifically bind to GBM cell line (U87MG cells) and particles without HA (LP, which do not bind to the GBM glioma cell line). FIG. 7B shows Representative FACS histograms of Particles comprising HA (HA-LP), which are bound to GBM patient and of control particles (LP) which do not bind the cells.

FIG. 8 GBM cells are resistant to chemotherapy treatment with DOX or BCNU. U87MG cells were treated with varying concentrations (1 μM, 10 μM and 100 μM) of Doxorubicin (DOX) and 1,3-bis(2-chloroethyl)-1-nitrosourea (BCNU). The bar graphs of FIG. 8 show the survivial of the cells, 48 hours after treatment.

FIG. 9A—show bar graphs of QPCR of Polo like Kinase (PLK1) gene expression in U87MG cells. The cells were incubated with liposomal particles comprising HA (HA-LNPs) or not comprising HA (LNPs-NH2) which further encapsulated either siRNA directed against Luciferase (siLuci) or siRNA directed against PLK1 (siPLK1) under shear flow conditions to simulate CSF flow. FIG. 9B—Pictogram showing Western blot analysis of PLK1 protein expression in the cells, after treatment with HA-LP containing siPLK1. Cells were harvested after 96-144 hr and analyzed for PLK1 protein levels using PLK1 antibody. β-Tubulin was used as a positive control. FIG. 9C—Bar graphs showing cell survival (as determined by XTT assay) under the various experimental conditions. Doxorubicin (DOX), was used as a positive control. * denotes p<0.001.

FIG. 11A—3 hours after administration; FIG. 11B—6 hours after administration and FIG. 11C—24 hours after administration, animals were sacrificed and Cy3-siRNA (light gray (originally red), one exemplary location is marked with arrow in each Figure) location was detected using confocal microscopy analysis. DAPI (gray, (originally Blue)), one exemplary location is marked with dashed arrow in each Figure) was used for nuclear staining. Bar scale −50 μm.

FIG. 12A—Bar graphs showing the percentage of PLK1 gene silencing by siRNA directed against PLK1, which is encapsulated/harbored within liposomal particles comprising HA that were administered to the tumor site of tumor bearing mice. The mice (n=10 mice/group) were treated twice by either mock transfection (Mock treated) or with the liposomal particles comprising HA (HA-LNPs) further harboring siRNA directed against Luciferase (siLuci) or siRNA directed against PLK1 (si-PLK1). Tumor cells were FACS sorted via a surface marker and PLK1 mRNA level was quantified using QPCR. * denotes p<0.001.

FIG. 12B and FIG. 12C show bar graphs of Cytokine (TNF-α, and IL-6) induction in microglia cells by siPLK1 entrapped in HA-LNPs. Mouse primary microglia cells were incubated at 37° C. for 6 h with siPLK1 entrapped in HA-LNPs at 0.05 and 0.5 mg/Kg siRNA. LPS (100 ng/mL) served as a positive control. The release of TNF-α (FIG.

12B), and IL-6 (FIG. 12C) to the medium was measured (pg/mL) by ELISA (R&D systems). Data is presented as the mean±SD of at least three independent experiments; and FIG. 12D Line graphs showing Kaplan-Meier survival analysis of GBM-bearing orthotropic U87MG cells (n=10/group) treated with siLuci (siControl), siPLK1 or saline. Overall 4 administrations were given at days 7 and 9 post tumor inoculation and then at days 20 and 22 post tumor inoculation.

DETAILED DESCRIPTION OF THE INVENTION

Definitions

Figure 1A:
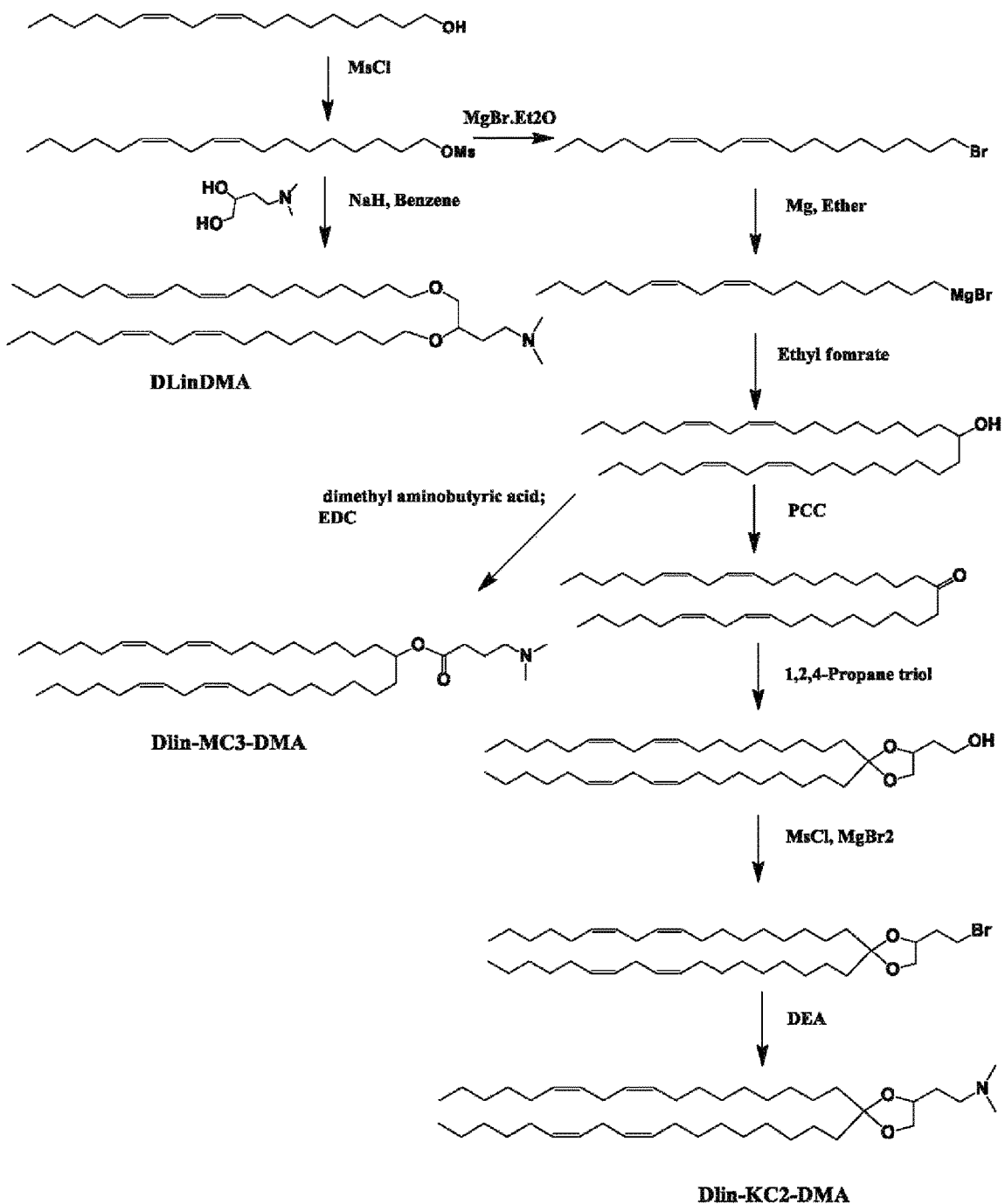
FIG. 1A: synthesis scheme of various synthetic cationic lipids used for the preparation of the cationic liposomes, according to some embodiments.

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "nucleic acid", "nucleic acid molecules" "oligonucleotide", "polynucleotide", and "nucleotide" may interchangeably be used herein. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, Antisense RNA, and the like. Each possibility is a separate embodiment. The terms further include oligonucleotides composed of naturally occurring bases, sugars, and covalent internucleoside linkages, as well as oligonucleotides having non-naturally occurring portions, which function similarly to respective naturally occurring portions.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "plurality" as used herein is directed to include more than one component.

The terms "Glycosaminoglycans" or "mucopolysaccharides" are directed to long unbranched polysaccharides consisting of a repeating disaccharide unit. The repeating unit may include a hexose (six-carbon sugar) or a hexuronic acid, linked to a hexosamine Members of the glycosaminoglycan family may vary in the type of hexosamine, hexose or hexuronic acid unit they contain (for example, glucuronic acid, iduronic acid, galactose, galactosamine, glucosamine) and in the geometry of the glycosidic linkage. The term Glycosaminoglycan includes natural, synthetic, or semisynthetic Glycosaminoglycan molecules. Exemplary Glycosaminoglycans include such Glycosaminoglycans as, but not limited to: Chondroitin sulfate, Dermatan sulfate, Keratan sulfate, Heparin, Heparan sulfate, Hyaluronan (also known as hyaluronic acid, hyaluronate, HA) and fragments, salts, and mixtures thereof. The term Glycosaminoglycan further includes Glycosaminoglycans that have been chemically modified by modifications such as, but not limited to: esterification, sulfation, polysulfation, and methylation. The glycosaminoglycans, except hyaluronic acid, are naturally in the form of a protein moiety bound covalently to a polysaccharide moiety. Methods for hydrolyzing the protein-sugar bond are well known to those skilled in the art, both chemically and enzymatically.

The terms "HA" and "Hyaluronan" refer to Hyaluronic acid that can be in a free form, and in an attached form, such as an extracellular matrix component. The Term HA further relates to any of its hyaluronate salts, including, for example, sodium hyaluronate, potassium hyaluronate, magnesium hyaluronate, and calcium hyaluronate. HA polysaccharide consists of alternating N-acetyl-D-glucosamine and D-glucuronic acid residues joined by alternating beta-1,3-glucuronidic and beta-1,4-glucosaminidic bonds. The HA may be of low molecular weight (for example, in the range of $MW=10^4$-$7.2\times10^4$) and/or of High molecular weight (for example, in the range of about $MW=3.1\times10^5$-$5\times10^6$ kDa). The HA may be of varying chain length. In some embodiments, the HA has a molecular weight of about 1 KDa-1000 KDa. In some embodiments, the HA has a molecular weight of about 5 KDa-850 KDa. In some embodiments, the HA has a molecular weight of about 7 KDa. In some embodiments, the HA has a molecular weight of about 800 kDa. Hyaluronic acid has a high affinity for the extracellular matrix and to a variety of tumors, including those of the breast, brain, lung, skin, and other organs and tissues. HA have high affinity of CD44 cellular receptors.

As used herein, the terms "cationic liposomes", "liposomes" and "lipid-based nanoparticle(s)" may interchangeably be used. The terms relate to the cationic liposomes of the present invention, which comprise/include/made of a lipid phase (also referred to herein as membranes) which includes a combination/plurality of lipids (selected from, but not limited to: cationic lipid(s), membrane stabilizing lipid(s), phosphatidylethanolamine(s), phospholipid(s)); Polyethylene glycol derivative(s), conjugated/bound to a lipid); further coated with an activated glycosaminoglycan bound to a PEG amine derivative of the liposome; and further encapsulate nucleic acid molecules. In some embodiments, the lipid based nanoparticles (liposomes) are multi-lamellar vesicles. In some embodiments, the lipid based nanoparticles are modified liposomes. In some embodiments, the lipid based nanoparticles may be used as an efficient delivery system to deliver nucleic acid molecules that are encapsulated therein, to a target site.

The term "construct", as used herein, refers to an artificially assembled or isolated nucleic acid molecule which may include one or more nucleic acid sequences, wherein the nucleic acid sequences may include coding sequences (that is, sequence which encodes an end product), regulatory sequences, non-coding sequences, or any combination thereof. The term construct includes, for example, vector but should not be seen as being limited thereto.

"Expression vector" refers to constructs that have the ability to incorporate and express heterologous nucleic acid fragments (such as, for example, DNA), in a foreign cell. In other words, an expression vector comprises nucleic acid sequences/fragments (such as DNA, mRNA, tRNA, rRNA), capable of being transcribed. Many prokaryotic and eukaryotic expression vectors are known and/or commercially available. Selection of appropriate expression vectors is within the knowledge of those having skill in the art. In some exemplary embodiments, the expression vector may encode for a double stranded RNA molecule in the target site.

The term "expression", as used herein, refers to the production of a desired end-product molecule in a target cell. The end-product molecule may include, for example an RNA molecule; a peptide or a protein; and the like; or combinations thereof.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. The transfection of the cell may be performed on any type of cell, of any origin, such as, for example, human cells, animal cells, plant cells, virus cell, and the like. The cells may be selected from isolated cells, tissue cultured cells, cell lines, cells present within an organism body, and the like.

As referred to herein, the term "target site" refers to the location in which the nucleic acid is directed to and/or the site in which the nucleic acid is to exert its biological effect. In some exemplary embodiments, the target site is a cell that may be selected from, but not limited to: a culture cell (primary cell or cell-line derived cell), and a cell within an organism body; a tissue, an organ, a microorganism (such as, for example, virus, bacteria, parasite), and the like. The organism may be any organism, such as, but not limited to: a mammal, such as human or an animal, an animal which is not a mammal (such as, for example, avian, Fish, and the like), and the like. In some exemplary embodiments, the target site is a subcellular location or cellular organelle (such as, for example, nucleus, cytoplasm, and the like). In some embodiments, the target site comprises a CD44 receptor.

The term "treating" and "treatment" as used herein refers to abrogating, inhibiting, slowing or reversing the progression of a disease or condition, ameliorating clinical symptoms of a disease or condition or preventing the appearance of clinical symptoms of a disease or condition. The term "preventing" is defined herein as barring a subject from acquiring a disorder or disease or condition.

The term "treatment of cancer" is directed to include one or more of the following: a decrease in the rate of growth of the cancer (i.e. the cancer still grows but at a slower rate); cessation of growth of the cancerous growth, i.e., stasis of the tumor growth, and, the tumor diminishes or is reduced in size. The term also includes reduction in the number of metastases, reduction in the number of new metastases formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like.

As used herein, the term "about" refers to +/−10%.

According to some embodiments of the present invention, there is provided a liposome for delivery of a nucleic acid, which comprises a lipid phase (membranes) comprising a plurality of lipids (including cationic lipid(s), membrane stabilizing lipid(s) and optionally additional lipids, such as, but not limited to, ionized lipids and/or phosphatidylethanolamine(s)), and PEG-Amine derivative (conjugated to a lipid); further coated with activated glycosaminoglycan conjugated to the PEG amine derivative of the particle, and further encapsulating a nucleic acid. In some embodiments, additional PEG derivatives may be included in the particle. In some embodiments, the liposomes may be used as an efficient delivery system to deliver a nucleic acid molecule to a desired target site. The target site may include any target site, such as, but not limited to: a cell, a tissue, an organ, a microorganism, and the like. The target site may be an in-vivo or in-vitro target site.

According to some embodiments, there is provided a cationic liposome for delivery of a nucleic acid, comprising: a) a lipid membrane comprising a cationic lipid, a membrane stabilizing lipid and PEG-amine conjugated to a lipid; b) a nucleic acid encapsulated within the liposome; and c) a glycosaminoglycan bound to the PEG amine derivative and coating the external surface of the liposome.

According to some embodiments, the present invention provides liposomes comprising a plurality of lipids comprising a cationic lipid, a membrane stabilizing lipid and at least one lipid conjugated to a polyethylene glycol (PEG) derivative, wherein the particles are coated with glycosaminoglycan molecules, bound to the PEG derivative. According to some embodiments the PEG derivative bears a PEG-amine. In some embodiments, the liposome encapsulate/carry nucleic acid molecules.

According to additional embodiments, the present invention provides a composition comprising a plurality of liposomes, the liposomes comprising a lipid phase comprising a plurality of lipids comprising a cationic lipid, a membrane stabilizing lipid and at least one lipid conjugated to a polyethylene glycol (PEG)-Amine derivative, wherein the particles are coated with glycosaminoglycan molecules, bound to the PEG-amine derivative; and further encapsulate/carry a nucleic acid.

According to yet additional embodiments, the present invention provides a composition comprising a plurality of liposomes, comprising a plurality of lipids comprising a cationic lipid, a membrane stabilizing lipid and at least one lipid conjugated to a polyethylene glycol (PEG)-Amine derivative, wherein the particles are coated with glycosaminoglycan molecules, bound to the PEG derivative and further comprising a nucleic acid molecule encapsulated within the lipid structure of the liposome.

Figure 1B:
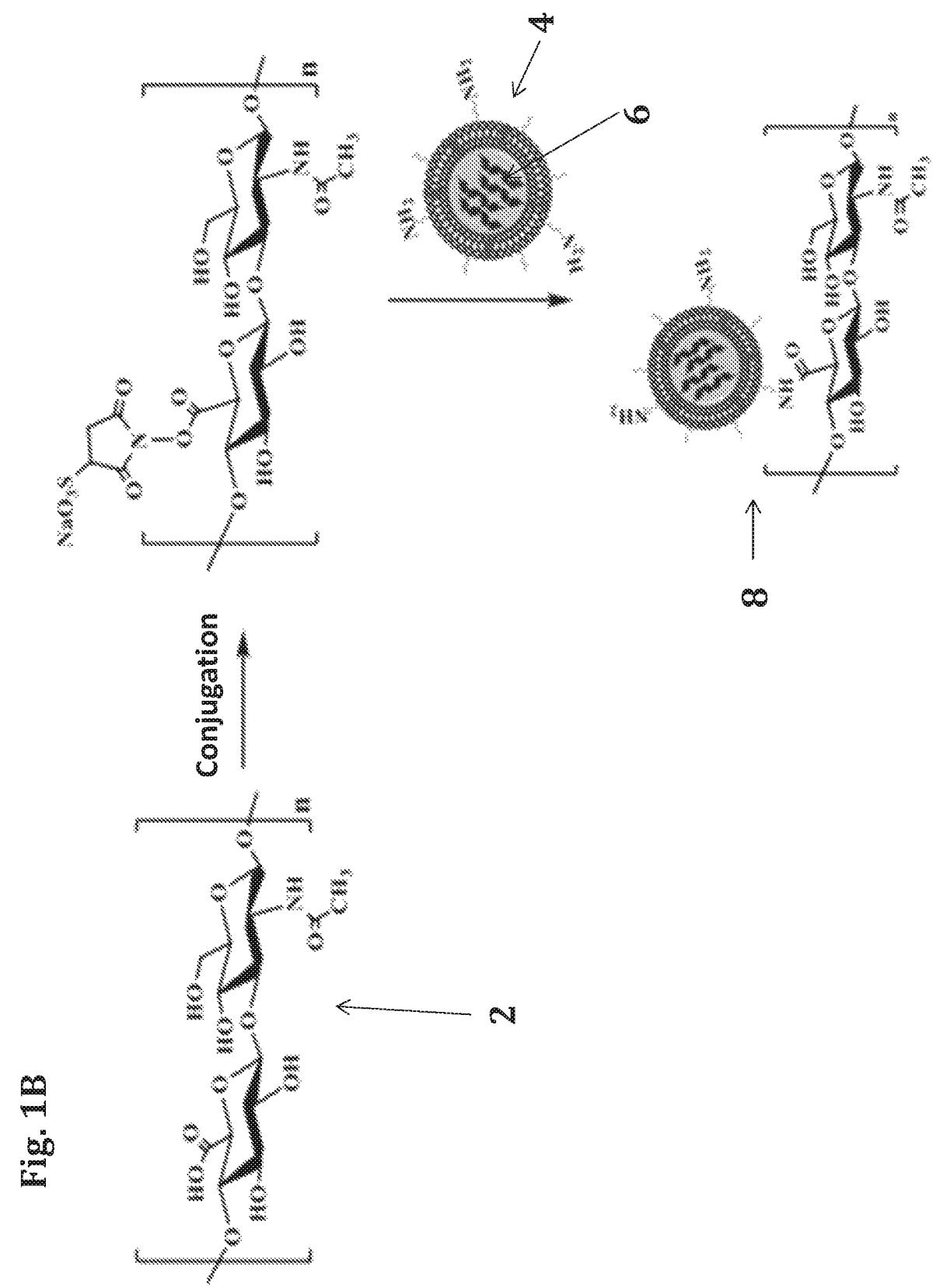
FIG. 1B: Schematic illustration of conjugation of glycosaminoglycan (exemplified as Hyaluronic acid (HA), 4)) to the liposomal particles (2), which encapsulate nucleic acid molecules (6), to form the coated particles (8), according to some embodiments.

Reference is now made to FIG. 1B, which is a schematic illustration of conjugation of glycosaminoglycan (exemplified as Hyaluronic acid (HA), 4)) to the liposomal particles (2), which encapsulate nucleic acid molecules (6), to form the coated liposomal particles (8), according to some embodiments. Further shown are the $NH_2$ residues which can interact with the activate glycosaminoglycan.

According to some exemplary embodiments, the plurality of lipids of the lipid phase (membranes) of the liposome may be of natural or synthetic source and may be selected from, but not limited to: cationic lipids, phosphatidylethanolamines, ionized lipids, membrane stabilizing lipids, phospholipids, and the like, or combinations thereof.

In some embodiments, the cationic lipids may be synthetic cationic lipids. In some embodiments, the cationic lipids may be selected from, but not limited to: DLinDMA, DLin-MC3-DMA and DLin-KC2-DMA; monocationic lipid N-[1-(2,3-Dioleoyloxy)]-N,N,N-trimethylammonium propane (DOTAP), BCAT 9'Z-octadecadienyl)-glycerol)-3-N-(bis-2-aminoethyl)-carbamate, BGSC (Bis-guanidinium-spermidine-cholesterol), BGTC (Bis-guanidinium-tren-cholesterol), CDAN (N'-cholesteryl oxycarbony 1-3,7-diazanonane-1,9-diamine), CHDTAEA (Cholesteryl hemidithiodiglycolyl tris(amino(ethyl)amine), DCAT (O-(1, 2-di-O-(9'Z-octadecanyl)-glycerol)-3-N-(bis-2-amino-ethyl)-carbamate), DC-Chol (3β [N—(N',N'-dimethylamin-oethane)-carbamoyl] cholesterol), DLKD (O,O'-Dilauryl N-lysylaspartate), DMKD (O,O'-Dimyristyl N-lysylaspartate), DOG (Diolcylglycerol, DOGS (Dioctadecylamidogly-cylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl succinyl paromomycin), DOST (Dioleyl succinyl tobramycin), DOTAP (1,2-Uiolcoyl-3-trimethyl ammoniopropane), DOTMA (N'[1-(2,3-Dioleyloxy)propyl]-N,N,N-trimethy-lammonium chloride), DPPES (Di-palmitoyl phosphatidyl ethanolamidosperminc), DDAB and DODAP. Each possibility is a separate embodiment.

In some exemplary embodiments, the cationic lipid has a pKa in the range of about 6.5-7. In some embodiments, the cationic lipid is selected from, but not limited to: DLinDMA, (with lipid pKa of 6.8), DLin-MC3-DMA (with lipid pKa of 6.44) and DLin-KC2-DMA (with lipid pKa of 6.7), or combinations thereof. Each possibility is a separate embodiment.

In some embodiments, the membrane stabilizing lipids may be selected from, but not limited to: cholesterol, phospholipids (such as, for example, phosphatidylcholine, phosphatidylethanolamine, phosphatidylinositol, phosphatidylserine, phosphatidylglycerol, diphosphatidylglycerols), cephalins, sphingolipids (sphingomyelins and glycosphingolipids), glycoglycerolipids, and combinations thereof. Each possibility is a separate embodiment.

In some embodiments, the Phosphatidylethanolamines may be selected from, but not limited to: 1,2-dilauroyl-L-phosphatidyl-ethanolamine (DLPE), 1,2-Dioleoyl-sn-glycero-3-phosphoethanolamine (DOPE), 1,2-Diphytanoyl-sn-glycero-3-phosphoethanolamine (DPhPE), 1,3-Dipalmitoyl-sn-glycero-2-phosphoethanolamine (1,3-DPPE), 1-Palmitoyl-3-oleoyl-sn-glycero-2-phosphoethanolamine (1,3-POPE), Biotin-Phosphatidylethanolamine, 1,2-Dimyristoyl-sn-glycero-3-phosphoethanolamine (DMPE), Dipalmitoylphosphatidylethanolamine (DPPE), 1,2-Distearoyl-sn-glycero-3-phosphoethanolamine (DSPE) or combinations thereof. In some embodiments, the Phosphatidylethanolamines may be conjugated to a PEG-Amine derivative. Each possibility is a separate embodiment.

According to some embodiments, the liposomes (lipid phase thereof), may further include additional PEG derivatives, in addition to a PEG-Amine derivative. In some embodiments, the PEG derivatives may be conjugated to one or more additional molecules, such as, a lipid. In some embodiments, the PEG derivative is selected from, but not limited to: PEG-DMG, cDMA 3-N-(-methoxy poly(ethylene glycol)2000)carbamoyl-1,2-dimyristyloxy-propylamine; PEG-cDSA, 3-N-(-methoxy poly(ethylene glycol)2000)carbamoyl-1,2-distearyloxy-propylamine, or combinations thereof. Each possibility is a separate embodiment.

In some embodiments, the PEG-Amine, conjugated to a lipid, provides a primary amine to which an activated glycosaminoglycan may be covalently attached.

According to some embodiments, the ratio between the various lipids may vary. In some embodiments, the ratio is a molar ratio. In some embodiments, the ratio is a weight ratio. In some embodiments, each of the lipid groups may be at molar ratio/a weight ratio of about 1%-99%.

According to some embodiments, the weight ratio between the nucleic acid and the lipid phase may be adjusted so as to achieve maximal biological effect by the nucleic acid on the target site. In some embodiments, the ratio between the nucleic acid and the lipid phase may be 1:1. For example, the weight ratio between the nucleic acid and the lipid phase may be 1:2. For example, the weight ratio between the nucleic acid and the lipid phase may be 1:5. For example, the weight ratio between the nucleic acid and the lipid phase may be 1:10. For example, the weight ratio between the nucleic acid and the lipids phase may be 1:16. For example, the weight ratio between the nucleic acid and the lipid phase may be 1:20. In some embodiments, the weight ratio between the nucleic acid and the lipid phase is about 1:5 to 1:20 (w:w).

According to some embodiments, the glycosaminoglycan used in preparation of the liposomes may include any unmodified and/or modified glycosaminoglycan. In some embodiments, the glycosaminoglycan may be selected from, but not limited to: HA, Chondroitin sulfate, Dermatan sulfate, Keratan sulfate, Heparin, Heparan sulfate, and salts thereof. The glycosaminoglycan may be of varying lengths. In some exemplary embodiments, the glycosaminoglycan is a high molecular weight (HMW) HA. In some exemplary embodiments, the glycosaminoglycan is a low molecular weight (LMW) HA. In other exemplary embodiments, the glycosaminoglycan is a combination of HA having varying molecular weights. In some embodiments, the HA has a molecular weight of about 3-20 KDa (for example, 7 KDa). In some embodiments, the HA has a molecular weight of about 600-1000 KDa (for example, 800 KDa). According to some embodiments, the Glycosaminoglycan may be activated prior to being reacted with the PEG-amine derivative of the lipid phase of the liposomes. For example, activation may include, but not limited to, acidifying the glycosaminoglycan, adding a crosslinker to the glycosaminoglycan, and the like. In exemplary embodiments, the crosslinker may be a carbodiimide selected from, but not limited to: EDC (EDAC, EDCI, 1-ethyl-3-(3-dimethylaminopropyl) carbodiimide), DCC (N,N'-dicyclohexylcarbodiimide), and DIC (N,N'-diisopropylcarbodiimide).

According to further embodiments, additional molecules/moieties/derivatives may be attached first to the glycosaminoglycan, prior to being reacted with the PEG-amine derivative of the liposomes. The additional molecules may be, for example, antibodies, folate, porphyrins, or lectins, and may be used for targeting of the liposomes to specific target sites. In additional embodiments, the additional targeting molecules/derivatives may be attached directly to the liposomes.

In some embodiments, the liposomes (including the glycosaminoglycan coating and a nucleic acid encapsulated within) have a particle size (diameter) in the range of about 5 to about 500 nm. In some embodiments, the liposomes have a particle size (diameter) in the range of about 10 to about 350 nm. In some embodiments, the liposomes have a particle size (diameter) in the range of about 50 to about 250 nm. In some embodiments, the liposomes have a particle size (diameter) in the range of about 10 to about 200 nm. In some embodiments, the liposomes have a particle size (diameter) in the range of about 20 to about 200 nm. In some embodiments, the liposomes have a particle size (diameter)

in the range of about 50 to about 200 nm. In some embodiments, the liposomes have a particle size (diameter) in the range of about 75 to about 200 nm. In some embodiments, the liposomes have a particle size (diameter) in the range of about 90 to about 200 nm. In some embodiments, the liposomes have a particle size (diameter) in the range of about 100 to about 200 nm. In some embodiments, the liposomes have a particle size (diameter) in the range of about 120 to about 200 nm. In some embodiments, the liposomes have a particle size (diameter) in the range of about 150 to about 200. In some embodiments, the liposomes have a particle size (diameter) in the range of about 50 to about 150 nm. In some embodiments, the liposomes have a particle size (diameter) in the range of over about 10 nm. In some embodiments, the liposomes have a particle size (diameter) of over about 20 nm. In some embodiments, the liposomes have a particle size (diameter) of over about 30 nm. In some embodiments, the liposomes have a particle size (diameter) of over about 40 nm. In some embodiments, the liposomes have a particle size (diameter) of over about 50 nm. In some embodiments, the liposomes have a particle size (diameter) of over about 60 nm. In some embodiments, the liposomes have a particle size (diameter) of over about 70 nm. In some embodiments, the liposomes have a particle size (diameter) of over about 80 nm. In some embodiments, the liposomes have a particle size (diameter) of over about 90 nm. In some embodiments, the liposomes have a particle size (diameter) of over about 100 nm. In some embodiments, the liposomes have a particle size (diameter) of over about 110 nm. In some embodiments, the liposomes have a particle size (diameter) of over about 120 nm. In some embodiments, the liposomes have a particle size (diameter) of over about 130 nm. In some embodiments, the liposomes have a particle size (diameter) of over about 140 nm. In some embodiments, the liposomes have a particle size (diameter) of over about 150 nm. In some embodiments, the liposomes have a particle size (diameter) of over about 160 nm. In some embodiments, the liposomes have a particle size (diameter) of over about 170 nm. In some embodiments, the liposomes have a particle size (diameter) of over about 180 nm. In some embodiments, the liposomes have a particle size (diameter) of over about 190 nm. In some embodiments, the liposomes have a particle size (diameter) of not more than about 500 nm.

According to exemplary embodiments, the liposomes may be comprised of a cationic lipid (such as, for example, DLinDMA, DLinMC3 or DlinKC2-DMA), cholesterol, 1,2-Distearoyl-sn-glycero-3-phosphocholine (DSPC), PEG derivative (such as DMG-PEG) and PEG-Amine conjugated to a lipid (such as PE-PEG-Amine); at various mol:mol ratios, and coated with HA of low and/or higher molecular weight (such as, 3-10 KDa (for example, 7 KDa) and/or 500-1000 KDa (for example, 800 KDa)). For example, the lipid phase may be comprised of: DLinDMA/Chol/DSPC/DMG-PEG/PE-PEG-Amine (mol/mol 40:40:18:1.5:0.5). For example, the lipid phase may be comprised of: DLinDMA/Chol/DSPC/DMG-PEG/PE-PEG-Amine (mol/mol 40:40:15:3:2). For example, the lipid phase may be comprised of: DLinMC3-DMA/Chol/DSPC/DMG-PEG/PE-PEG-Amine (mol/mol 40:40:18:1.5:0.5). For example, the lipid phase may be comprised of: DLinMC3-DMA/Chol/DSPC/DMG-PEG/PE-PEG-Amine (mol/mol 40:40:15:3:2). For example, the lipid phase may be comprised of: DLin-KC2-DMA/Chol/DSPC/DMG-PEG/PE-PEG-Amine (mol/mol 40:40:18:1.5:0.5). For example, the lipid phase may be comprised of: DLinKC2-DMA/Chol/DSPC/DMG-PEG/PE-PEG-Amine (mol/mol 40:40:15:3:2).

According to some embodiments, the lipid phase may comprise about 30-60% (mol:mol) cationic lipids. For example, the cationic lipid(s) may comprise about 40-50% (mol:mol) of the lipid phase.

According to some embodiments, the lipid phase may comprise about 20-70% (mol:mol) membrane stabilizing lipids. For example, the membrane stabilizing lipids may comprise about 40-60% of the lipid phase. In some embodiments, more than one type of membrane stabilizing lipid may be used in the lipid phase. For example, the membrane stabilizing lipid may include cholesterol (being about 30-50% (mol:mol) of the lipid phase), and a phospholipid (such as, for example, DSPC), that may be about 5-15% (mol:mol) of the lipid phase.

According to some embodiments, the lipid phase may comprise about 0.25-3% (mol:mol) of PEG-amine (conjugated to a lipid). For example, the PEG-amine may comprise about 0.5-1.5% of the lipid phase.

According to some embodiments, if present, an additional PEG-derivative (conjugated to a lipid) may comprise about 0.5-10% of the lipid phase composition. For example, the additional PEG derivative may comprise about 1.5-5% of the lipid phase.

According to some embodiments, there is provided a method for the preparation of a glycosaminoglycan coated liposome for delivery of a nucleic acid, the method comprising one or more of the steps of:
 a) forming a lipid phase comprising the step of mixing cationic lipid, membrane stabilizing lipid and PEG-Amine conjugated to a phospholipid, in an organic solvent at a desired ratio and forming a lipid mixture,
 b) generating the liposome by the step of:
  introducing a nucleic acid in an aqueous solution into the lipid mixture of step a); and
 c) adding an activated glycosaminoglycan to the mixture.

In some embodiments, the lipids are suspended in an acidic aqueous buffer.

According to some embodiments, there is provided a method for the preparation of a glycosaminoglycan coated liposome for delivery of a nucleic acid, the method comprising one or more of the steps of:
 a) forming a lipid phase comprising the steps of:
  i) mixing cationic lipid, membrane stabilizing lipid and PEG-Amine conjugated to a lipid, in an organic solvent at a desired ratio and forming a lipid mixture,
  ii) suspending the lipid mixture in a buffer to generate multilamellar vesicles;
 b) activation of a glycosaminoglycan, comprising: i) dissolving a glycosaminoglycan in an acidic buffer and adding a crosslinker to form an activated glycosaminoglycan; and
 c) generating the liposome by the steps of:
  i) incubating/mixing/suspending the lipid phase of step a) with the nucleic acid; and
  ii) adding the activated glycosaminoglycan to the mixture.

In some embodiments, the lipids are suspended in an acidic aqueous buffer. In some embodiments, the acidic aqueous buffer is selected from, but not limited to: MES Buffer (for example, 50 mM-100 mM, pH 5.5), Acetate buffer (for example, 100 mM, pH 4.0), and the like. In some embodiments, the nucleic acid may be added in an acidic buffer, such as, for example, but not limited to: MES Buffer (for example, 50 mM-100 mM, pH 5.5), Acetate buffer (for example, 100 mM, pH 4.0). In some embodiments, the nucleic acid may be mixed with the lipids, prior to formation of the multilamellar vesicles. In such embodiment, the nucleic acid (for example, in acetate buffer) and the lipids (for example, in 100% ethanol) may both be introduced to a microfluidizer mixer to form the particles encapsulating the nucleic acid.

According to some embodiments, the method for the preparation of the liposomes may include various modifications to finely adjust the components of the composition, as well as the ratio between the components, so as to obtain the most effective composition. The modifications may include, for example, such parameters as, but not limited to: the specific lipids used for the formation of the lipid composition, the ratio between the lipids of the lipid compositions, the identity of the nucleic acid to be encapsulated, the ratio between the nucleic acid and the lipid composition, the specific glycosaminoglycan used, the ratio between the glycosaminoglycan and the lipid composition, the pH at which reactions are performed, the temperatures at which reactions are performed, the conditions at which the reactions are formed, the time length of various steps, and the like, or any combination thereof.

According to some embodiments, the method for the preparation of the liposomes of the present invention may beneficially result in uniformly distributed lipid composition particle size.

According to some embodiments, the liposomes formed by the methods of the present invention may be lyophilized or dehydrated at various stages of formation.

According to some embodiments, the liposomes of the present disclosure (i.e., including a glycosaminoglycan coating and nucleic acid encapsulated within) can be used in the treatment of various pathological conditions in an organism in need thereof.

According to some embodiments, the liposomes may be administered as is. In some embodiments, the liposomes may be administered in a solution. In some embodiments, the liposomes may be formulated to a suitable pharmaceutical composition to be administered by any desired route of administration. Exemplary routes of administration include such routes as, but not limited to: topical, oral or parenteral. Depending on the intended mode of administration, the compositions used may be in the form of solid, semi-solid or liquid dosage forms, such, as for example, tablets, suppositories, pills, capsules, powders, liquids, suspensions, or the like, preferably in unit dosage forms suitable for single administration of precise dosages. The pharmaceutical compositions may include the cationic liposomes, a pharmaceutical acceptable excipient, and, optionally, may include other medicinal agents, pharmaceutical agents, carriers, adjuvants, and the like. It is preferred that the pharmaceutically acceptable carrier be one which is inert to the nucleic acid encapsulated within the particles and which has no detrimental side effects or toxicity under the conditions of use. In some embodiments, the administration is localized.

In some embodiments, injectable formulations for parenteral administration can be prepared as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, and the like. Aqueous injection suspensions may also contain substances that increase the viscosity of the suspension, including, for example, sodium carboxymethylcellulose, sorbitol, and/or dextran. Optionally, the suspension may also contain stabilizers. The parenteral formulations can be present in unit dose or multiple dose sealed containers, such as ampules and vials, and can be stored in a freeze-dried (lyophilized) condition requiring only the addition of the sterile liquid carrier, such as, for example, water, for injections immediately prior to use. In some embodiments, parenteral administration includes intravenous administration.

In other embodiments, for oral administration, a pharmaceutically acceptable, non-toxic composition may be formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained release formulations and the like. Formulations suitable for oral administration can consist of liquid solutions such as effective amounts of the compound(s) dissolved in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, (such as, for example ethanol, benzyl alcohol, and the polyethylene alcohols), either with or without the addition of a pharmaceutically acceptable surfactant, suspending agents, or emulsifying agents.

In determining the dosages of the liposomes to be administered, the dosage and frequency of administration is selected in relation to the pharmacological properties of the specific biologically active agent encapsulated within the particles.

In some exemplary embodiments, a liposome of the invention comprising a nucleic acid may be used in the treatment of various pathological conditions, depending on the identity of the nucleic acid, the target site, and the like. Exemplary pathological conditions may be selected from, but not limited to: various types of cancer, various infections (such as, for example, viral infection, bacterial infection, fungal infection, and the like), autoimmune diseases, neurodegenerative diseases, inflammations (for example, inflammatory bowel diseases such as Crohn's disease, colitis, and the like), eye related syndromes and diseases, pulmonary related diseases, gastro-intestinal related syndromes and diseases, and the like.

In some exemplary embodiments, a liposome comprising a nucleic acid, such as, for example, siRNA, miRNA, shRNA, and the like, may be used in the treatment of various pathological conditions, depending on the identity of the nucleic acid, the target site, and the like. In some embodiments, the nucleic acid encapsulated within the liposome may be a nucleic acid capable of inducing silencing of a target gene. In some embodiments, the target gene may be any gene, the expression of which is related to the condition to be treated. In some embodiments, the target gene may be a gene selected from, but not limited to: growth factors (such as EGFR, PDGFR), genes related to angiogenesis pathways (such as VEGF, Integrins), genes involved in intracellular signaling pathways and cell cycle regulation (such as PI3K/AKT/mTOR, Ras/Raf/MAPK, PDK1, CHK1, PLK1, Cyclins). In some embodiments, a combination of nuciciec acids, each having one or more targtes may be encapsulated within the liposomal particles.

According to some embodiments, exemplary pathological conditions that may be treated by the liposome particles comprising a nucleic acid may be selected from, but not limited to: various types of cancer, various infections (such as, for example, viral infection, bacterial infection, fungal infection, and the like), autoimmune diseases, neurodegenerative diseases, inflammations (for example, inflammatory bowel diseases such as Crohn's disease, colitis, and the like), eye related syndromes and diseases, pulmonary related diseases, gastro-intestinal related syndromes and diseases, and the like.

In some exemplary embodiments, the liposomes comprising a nucleic acid (such as, siRNA or miRNA or shRNA), may be used for the treatment of cancer. Cancer is a disorder in which a population of cells has become, in varying degrees, unresponsive to the control mechanisms that normally govern proliferation and differentiation. Cancer refers to various types of malignant neoplasms and tumors, including metastasis to different sites. Non-limiting examples of cancers which can be treated by the lipid-based compositions are ovarian cancer, prostate cancer, breast cancer, skin cancer, melanoma, colon cancer, lung cancer, pancreatic cancer, gastric cancer, bladder cancer, Ewing's sarcoma, lymphoma, leukemia, multiple myeloma, head and neck cancer, kidney cancer, bone cancer, liver cancer and thyroid cancer. Specific examples of cancers include such types as, but not limited to: adenocarcinoma, adrenal gland tumor, ameloblastoma, anaplastic tumor, anaplastic carcinoma of the thyroid cell, angiofibroma, angioma, angiosarcoma, apudoma, argentaffinoma, arrhenoblastoma, ascites tumor cell, ascitic tumor, astroblastoma, astrocytoma, ataxia-telangiectasia, atrial myxoma, basal cell carcinoma, bone cancer, bone tumor, brainstem glioma, brain tumor, breast cancer, Burkitt's lymphoma, carcinoma, cerebellar astrocytoma, cervical cancer, cholangiocarcinoma, cholangioma, chondroblastoma, chondroma, chondrosarcoma, chorioblastoma, choriocarcinoma, colon cancer, common acute lymphoblastic leukemia, craniopharyngioma, cystocarcinoma, cystofibroma, cystoma, cytoma, cutaneous T-cell lymphoma, ductal carcinoma in situ, ductal papilloma, dysgerminoma, encephaloma, endometrial carcinoma, endothelioma, ependymoma, epithelioma, erythroleukaemia, Ewing's sarcoma, extra nodal lymphoma, feline sarcoma, fibroadenoma, fibrosarcoma, follicular cancer of the thyroid, ganglioglioma, gastrinoma, glioblastoma multiforme, glioma, gonadoblastoma, haemangioblastoma, haemangioendothelioblastoma, haemangioendothelioma, haemangiopericytoma, haematolymphangioma, haemocytoblastoma, haemocytoma, hairy cell leukemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angiofibroma, Kaposi sarcoma, kidney tumor, large cell lymphoma, leukemia, chronic leukemia, acute leukemia, liver cancer, liver metastases, Lucke carcinoma, lymphadenoma, lymphangioma, lymphocytic leukemia, lymphocytic lymphoma, lymphocytoma, lymphoedema, lymphoma, lung cancer, malignant mesothelioma, malignant teratoma, mastocytoma, medulloblastoma, melanoma, meningioma, mesothelioma, metastatic cancer, Morton's neuroma, multiple myeloma, myeloblastoma, myeloid leukemia, myelolipoma, myeloma, myoblastoma, myxoma, nasopharyngeal carcinoma, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteosarcoma, ovarian cancer, Paget's disease of the nipple, pancoast tumor, pancreatic cancer, phaeochromocytoma, pheochromocytoma, plasmacytoma, primary brain tumor, prolactinoma, renal cell carcinoma, retinoblastoma, rhabdomyosarcoma, rhabdosarcoma, solid tumor, sarcoma, secondary tumor, seminoma, skin cancer, small cell carcinoma, squamous cell carcinoma, T-cell lymphoma, teratocarcinoma, testicular cancer, thymoma, trophoblastic tumor, vestibular schwannoma, Wilm's tumor, or a combination thereof.

In some exemplary embodiments, the nucleic acid (such as, siRNA, miRNA or shRNA) that may be used for the treatment of cancer are directed against a target gene, which is involved in the regulation of cell cycle. In some exemplary embodiments, the target gene may be Polo-like Kinase 1 (PLK), Cyclin D1, CHK1, Notch pathway genes, PDGFRA, EGFRvIII, PD-L1, RelB, and the like.

According to some embodiments, there is thus provided a method for the treatment of cancer, comprising the step of administration to a subject in need thereof the liposomes of the present disclosure or a pharmaceutical compositions comprising the same. In some embodiments, there is provided the use of the liposomes of the present disclosure or a pharmaceutical composition comprising the same, for the treatment of cancer.

In some exemplary embodiments, the cancer is carcinoma. In some embodiments, the cancer is adeno-carcinoma.

In some embodiments, the cancer is Glioma. In some embodiments, the glioma is selected from: Astrocytoma (including juvenile pilocytic astrocytoma, low grade astrocytoma, anaplastic astrocytoma, or glioblastoma); Ependymoma; Mixed Glioma (Oligoastrocytoma); Oligodendroglioma; oligodendroglioma; Optic Glioma and Gliomatosis Cerebri. In some exemplary embodiments, the cancer is Grade IV Astrocytoma (Glioblastoma Multiforme (GBM)). In some embodiments, the GBM is chemo-resistant GBM.

In some embodiments, the liposomal particles of the present disclosure or a pharmaceutical compositions comprising the same, may be administered is a localized manned. For example, when treating GBM, the particles, or pharmaceutical compositions comprising the same may be administered directly to the GBM site.

In some embodiments, the localized administration of the particles or compositions comprising the same, into brain regions (such as, to primary neurosphers of GBM subjects) is able to withstand the flow of the cerebrospinal fluid and exert its effect by delivering a therapeutic nucleic acid to the target site.

In some embodiments, the liposomes of the present disclosure or a pharmaceutical composition comprising the same encapsulate therein an siRNA nucleic acid. In some embodiments, the siRNA is an siRNA molecule directed against Polo-like kinase 1 (PLK1) (that is, the siRNA is capable of reducing or eliminating expression of the PLK1 gene product). In some embodiments, the siRNA is an siRNA directed against a Notch pathway gene or PDGFRA for treating proneural GBM. In some embodiments, the siRNA is an siRNA directed against EGFRvIII for treating Classic GBM. In some embodiments, the siRNA is an siRNA directed against PD-L1 for treating mesenchymal GBM. In some embodiments, the siRNA is an siRNA directed against RelB (an oncogenic driver of tumor growth and invasion) for mesenchymal GBM.

In some embodiments, there is provided a method of treating GBM, the method comprising localized administration of the liposomes of the present disclosure or a pharmaceutical compositions comprising the same, wherein the liposomes encapsulate an siRNA nucleic acid directed against PLK1.

In some embodiments, there is provided a method of treating proneural GBM, the method comprising localized administration of the liposomes of the present disclosure or a pharmaceutical compositions comprising the same, wherein the liposomes encapsulate an siRNA nucleic acid directed against notch pathway genes of PDGFRA.

In some embodiments, there is provided a method of treating classic GBM, the method comprising localized administration of the liposomes of the present disclosure or a pharmaceutical compositions comprising the same, wherein the liposomes encapsulate an siRNA nucleic acid directed against EGFRvIII.

In some embodiments, there is provided a method of treating mesenchymal GBM, the method comprising localized administration of the liposomes of the present disclosure or a pharmaceutical compositions comprising the same, wherein the liposomes encapsulate an siRNA nucleic acid directed against PD-L1 and/or RelB.

In some embodiments, combinational treatment with multiple nucleic acid types encapsulated within the liposomes may be used to provide an enhanced beneficial effect.

In some embodiments, when treating a condition, administration of the liposomes carrying a nucleic acid may be performed in combination with one or more additional treatments. For example, when treating cancer, such combination therapy may be used to increase tumor susceptibility to chemotherapy and irradiation. In some exemplary embodiments, for treating cancer, silencing nucleic acids (such as, siRNA, miRNA, shRNA) that target genes such as, MGMT, Cx43, HeR1/EGF-R[46], VEGF[44], BCL-2 and Toll-like receptors may be used and may further provide synergistic responses. For example, targeting the MDR-1 (multi drug resistance) gene can increase anti-cancer drugs treatment efficiency, as this gene's overexpression is correlated with drug resistance in cancer, such as, GBM.

In some embodiments, when treating a condition, repeated administration of the liposomes carrying a nucleic acid may be performed, wherein the dosages administered and the composition of the nucleic acid encapsulated therein may be identical, similar or different. In some embodiments, the administration may be prolong (such as over the course of 1-120 hours).

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Preparation of Cationic Liposomes Encapsulating siRNA

Preparation of Cationic Lipids:

Three types of cationic lipids were synthesized: DLinDMA, DLin-MC3-DMA and DLin-KC2-DMA with lipid PKa of 6.7 (KC2 and MC3) and 6.8 (DLinDMA). Cationic lipids were synthesized essentially as summarized in FIG. 1.

DLinDMA: To a solution of 3-(Dimethylamino)-1,2-propanediol (140 mg, 1.2 mmol) and 95% sodium hydride (NaH, 322 mg, 20 mmol) were stirred in benzene (10 mL) under argon for 30 min. The mesyl ester of linoleic acid (1 g, 3 mmol) was added and the reaction refluxed under argon for 18 h. The reaction mixture was then cooled in an ice bath while quenching via the slow addition of ethanol. Following dilution with a further 50 mL of benzene, the mixture was washed with distilled water (2×100 mL) and brine (100 mL), using ethanol (~20 mL) to aid phase separation if necessary. The organic phase was dried over anhydrous sodium sulphate and evaporated. The crude product was purified on a silica gel column eluted with chloroform containing 0-5% methanol. Column fractions were analyzed by thin layer chromatography (TLC) (silica gel, chloroform/methanol 9:1 v/v) and fractions containing pure product were collected and concentrated to obtain 400 mg of pure product DLinDMA as pale yellow oil.

2,2-Dilinoleyl-4-(2-dimethylaminoethyl)-[1,3]-dioxolane (DLin-KC2-DMA)

Synthesis of Dilinoleyl Ketone: To a mixture of dilinoleyl methanol (2.0 g, 3.8 mmol) and anhydrous sodium carbonate (0.2 g) in 100 mL of $CH_2Cl_2$ was added pyridinium chlorochromate (PCC, 2.0 g, 9.5 mmol). The resulting suspension was stirred at room temperature for 60 minutes. Ether (300 mL) was then added into the mixture, and the resulting brown suspension was filtered through a pad of silica gel (300 mL). The silica gel pad was further washed with ether (3×200 mL). The ether filtrate and washes were combined. Evaporation of the solvent gave 3.0 g of an oily residual as a crude product. The crude product was purified by column chromatography on silica gel (230-400 mesh, 250 mL) eluted with 0-3% ether in hexanes. This gave 1.8 g (90%) of dilinoleyl ketone. Synthesis of 2,2-Dilinoleyl-4-(2-hydroxyethyl)-[1,3]-dioxolane: A mixture of dilinoleyl ketone (527 mg, 1.0 mmol); 1,2,4-butanetriol (technical grade, ca. 90%, 236 mg, 2 mmol); and pyridinium p-toluenesulfonate (50 mg, 0.2 mmol) in 50 mL of toluene was refluxed under nitrogen overnight with a Dean-Stark tube to remove water. The resulting mixture was cooled to room temperature. The organic phase was washed with water (2×30 mL), then brine (50 mL), and dried over anhydrous $Na_2SO_4$. Evaporation of the solvent resulted in a yellowish oily residual (0.6 g). The crude product was purified by column chromatography on silica gel (230-400 mesh, 100 mL) with dichloromethane as eluent. This afforded 0.5 g of pure 2,2-Dilinoleyl-4-(2-hydroxyethyl)-[1,3]-dioxolane. Synthesis of 2,2-Dilinoleyl-4-(2-methanesulfonylethyl)-[1,3]-dioxolane: To a solution of 1 (500 mg, 0.81 mmol) dry triethylamine (218 mg, 2.8 mmol) in 50 mL of anhydrous $CH_2Cl_2$ was added methane sulfonyl anhydride (290 mg, 1.6 mmol) under nitrogen. The resulting mixture was stirred at room temperature overnight. The mixture was diluted with 25 mL of $CH_2Cl_2$. The organic phase was washed with water (2×30 mL), then brine (50 mL), and dried over anhydrous Na2SO4. The solvent was evaporated to afford 510 mg of yellowish oil. The crude product (2,2-Dilinoleyl-4-(2-methanesulfonylethyl)-[1,3]-dioxolane) was used in the following step without further purification. To the above crude material, under nitrogen 20 mL of dimethylamine in THF (2.0 M) was added. The resulting mixture was stirred at room temperature for 6 days. An oily residual was obtained upon evaporation of the solvent. Column chromatography on silica gel (230-400 mesh, 100 mL) with 0-5% methanol gradient in dichloromethane as eluent resulted in 380 mg of the product DLin-KC2-DMA as pale oil.

The following cationic liposomes were prepared:
The following formulations (lipid phase compositions) were prepared in 100% Ethanol:
1. DLinDMA/Chol/DSPC/DMG-PEG/PE-PEG-Amine (mol/mol 40:40:18:1.5:0.5).
2. DLinDMA/Chol/DSPC/DMG-PEG/PE-PEG-Amine (mol/mol 40:40:15:3:2).
3. DLinMC3-DMA/Chol/DSPC/DMG-PEG/PE-PEG-Amine (mol/mol 40:40:18:1.5:0.5).
4. DLinMC3-DMA/Chol/DSPC/DMG-PEG/PE-PEG-Amine (mol/mol 40:40:15:3:2).
5. DLin-KC2-DMA/Chol/DSPC/DMG-PEG/PE-PEG-Amine (mol/mol 40:40:18:1.5:0.5).
6. DLinKC2-DMA/Chol/DSPC/DMG-PEG/PE-PEG-Amine (mol/mol 40:40:15:3:2).

(Chol=Cholesterol; DSPC=1,2-Distearoyl-sn-glycero-3-phosphocholine; DMG-PEG=1,2-Dimyristoyl-sn-glycerol, methoxypolyethylene Glycol; PE-PEG-Amine 1,2-distearoyl-sn-glycero-3-phosphoethanolamine-N-[amino(polyethylene glycol)].

The formulations listed above were prepared as follows: After carefully dissolving each lipid phase formulation in 100% Ethanol, while stirring, the lipids were added into 50 mM Sodium Acetate buffer, (pH 4) to generate multilamellar vesicles (total 33% Ethanol). The formed multilamellar vesicles were then extruded with 80 nm diameter filters (Whatman) into small unilamellar vesicles.

siRNAs molecules (1.5 mg/mL in acetate buffer pH 4.0—stock) at 1:16 (wt/wt) siRNA:Lipids ratio was added to form 33% Ethanol and 66% Acetate Buffer.

Alternatively, lipids were mixed with ethanol (100%), siRNAs molecules were resuspeneded in acetate buffer, and both were introduced to a microfluidizer mixer (Precision NanoSystems, Vancouver, BC) to form the particles. Briefly, one volume of lipid mixture, prepared in ethanol and three volumes of siRNA (1:16 w/w siRNA to lipid, containing acetate buffer solutions) were mixed using dual syringe pump (Model S200, kD Scientific, Holliston, Mass.) to drive the solutions through the micro mixer at a combined flow rate of 2 ml/minute (0.5 mL/min for ethanol and 1.5 mL/min for aqueous buffer).

The particles (prepared according to any of the preparation methods) were dialyzed against PBS pH 7.4 overnight to remove ethanol. In order to remove un-encapsulated siRNA, Amicon 100K MW cutoff or a Mono Q column were used.

Conjugation of Hyaluronic Acid (HA) to the Particles
Low and High MW sizes of HA (LifeCore) were used for the conjugation:
Low MW HA 5 kDa or 7 Kda
High MW HA—800 KDa HA was conjugated to the PEG amine by an amine coupling method: First, carboxylic groups of HA (Lifecore Biomedical LLC, USA) were activated by EDC/sulfo-NHS (1:1 ratio EDC:COOH, 1:1 ratio EDC/sulfo-NHS) in DIW for 1-2 h (HA (0.3 mg, 5×10$^5$ mmol) was dissolved in water and added with (0.2 mg, 10×10$^5$ mmol) and sulfo-NHS (0.3 mg, 10×10$^5$ mmol). The lipid particles (amine-functionalized particles) were then added in PBS (pH 7.8~8.2). The reaction continued for 2-3 h followed by dialysis against PBS (pH 7.4) at RT, for 24 hours, with a 12-14 KDa cutoff to remove excess HA and EDC and unbound small HA (5-7 KDa) or by three washings using ultracentrifugation to remove unbound 800 KDa HA. The ratio between HA to Amine was maintained at 5 to 1 (HA:Amine) The final HA/lipid ratio was typically 75 µg HA/µmole lipid as assayed by $^3$H-HA (ARC, Saint Louis, Mich.).

Example 2

Characterization of Various Cationic Liposomal Formulations siRNA Entrapment Efficiency Assay:
siRNA encapsulation efficiency was determined by the Quant-iT RiboGreen RNA assay (Invitrogen) as previously reported (Landeman-Milo et al. 2012 Cancer Letters and Peer D. et al. Science 2008). Briefly, the entrapment efficiency was determined by comparing fluorescence of the RNA binding dye RiboGreen in the different formulations samples, in the presence and absence of Triton X-100. In the absence of the detergent, fluorescence can be measured from accessible (unentrapped) siRNA only. Whereas, in the presence of the detergent, fluorescence is measured from total siRNA, thus, the % encapsulation is described by the equation:

% siRNA encapsulation=[1−(free siRNA conc./total siRNA conc.)]×100.

Transmission Electron Microscopy (TEM) Analysis. The particles were analyzed by transmission electron microscopy for their size and shape. A drop of aqueous solution containing LNPs (with or without HA) were placed on a carbon coated copper grid and air-dried. The analysis was carried out on Joel 1200 EX (Japan) transmission electron microscopy.

Scanning Electron Microscopy (SEM): Particles containing aqueous sample (with or without HA) were dried on silica wafer and analysis was carried out on Quanta 200 FEG (USA) scanning electron microscopy.

The results of the entrapment assay are presented in Table 1. The formulation of each composition is indicated.

TABLE 1

Physicochemical and structural analysis of the different formulations

| Formulation (composition of the particles) | Size (nm) | Polydispersity Index (PDI) | % siRNA entrapment/encapsulation |
|---|---|---|---|
| DLinDMA/Chol/DSPC/DMG-PEG/PE-PEG-Amine (mol/mol 40:40:18:1.5:0.5) | 129.2 | 0.08 | 95 |
| DLinDMA/Chol/DSPC/DMG-PEG/PE-PEG-Amine (mol/mol 40:40:18:1.5:0.5) - coated with 7 KDa HA | 175.9 | 0.201 | 96 |
| DLinDMA/Chol/DSPC/DMG-PEG/PE-PEG-Amine (mol/mol 40:40:18:1.5:0.5) - coated with 800 KDa HA | 192.3 | 0.245 | 95 |

TABLE 1-continued

Physicochemical and structural analysis of the different formulations

| Formulation (composition of the particles) | Size (nm) | Polydispersity Index (PDI) | % siRNA entrapment/ encapsulation |
|---|---|---|---|
| DLinDMA/Chol/DSPC/DMG-PEG/PE-PEG-Amine (mol/mol 40:40:15:3:2) | 113.3 | 0.05 | 95 |
| DLinDMA/Chol/DSPC/DMG-PEG/PE-PEG-Amine (mol/mol 40:40:15:3:2) coated with 7 KDa HA | 189.4 | 0.224 | 94 |
| DLinDMA/Chol/DSPC/DMG-PEG/PE-PEG-Amine (mol/mol 40:40:15:3:2) coated with 800 KDa HA | 194.6 | 0.243 | 97 |
| DLinMC3-DMA/Chol/DSPC/DMG-PEG/PE-PEG-Amine (mol/mol 40:40:18:1.5:0.5) | 117.40 | 0.067 | 94 |
| DLinMC3-DMA/Chol/DSPC/DMG-PEG/PE-PEG-Amine (mol/mol 40:40:18:1.5:0.5)-HA (7 KDa) | 145.5 | 0.134 | 91 |
| DLinMC3-DMA/Chol/DSPC/DMG-PEG/PE-PEG-Amine (mol/mol 40:40:18:1.5:0.5)-HA (800 KDa) | 190.5 | 0.223 | 92 |
| DLinMC3-DMA/Chol/DSPC/DMG-PEG/PE-PEG-Amine (mol/mol 40:40:15:3:2) | 104.9 | 0.045 | 94 |
| DLinMC3-DMA/Chol/DSPC/DMG-PEG/PE-PEG-Amine (mol/mol 40:40:15:3:2)- HA (7 KDa) | 123.4 | 0.123 | 92 |
| DLinMC3-DMA/Chol/DSPC/DMG-PEG/PE-PEG-Amine (mol/mol 40:40:15:3:2)- HA (800 KDa) | 197.5 | 0.223 | 94 |
| DLin-KC2-DMA/Chol/DSPC/DMG-PEG/PE-PEG-Amine (mol/mol 40:40:18:1.5:0.5) | 89.40 | 0.03 | 98 |
| DLin-KC2-DMA/Chol/DSPC/DMG-PEG/PE-PEG-Amine (mol/mol 40:40:18:1.5:0.5)-HA (7 KDa) | 108.4 | 0.118 | 98 |
| DLin-KC2-DMA/Chol/DSPC/DMG-PEG/PE-PEG-Amine (mol/mol 40:40:18:1.5:0.5)-HA (800 KDa) | 174.4 | 0.149 | 98 |
| DLin-KC2-DMA/Chol/DSPC/DMG-PEG/PE-PEG-Amine (mol/mol 40:40:15:3:2) | 78.9 | 0.045 | 98 |
| DLin-KC2-DMA/Chol/DSPC/DMG-PEG/PE-PEG-Amine (mol/mol 40:40:15:3:2)- HA (7 KDa) | 110.4 | 0.109 | 97 |
| DLin-KC2-DMA/Chol/DSPC/DMG-PEG/PE-PEG-Amine (mol/mol 40:40:15:3:2)- HA (800 KDa) | 175.4 | 0.229 | 96 |
| DLinMC3-DMA/DSPC/Chol/DMG-PEG/DCPE-PEG-Amine (mol/mol 50:10:38:18:1.5:0.5) | 79 ± 3 | 0.13 | 94 ± 4 |
| DLinMC3-DMA/DSPC/Chol/DMG-PEG/DCPE-PEG-Amine (mol/mol 50:10:38:18:1.5:0.5)-HA (5 KDa) | 100.7 ± 3 | 0.2 | 80 ± 11 |

The results suggest a very high percentage (over 91%) of entrapment of the nucleic acid molecule within the particles.

Figure 2A:
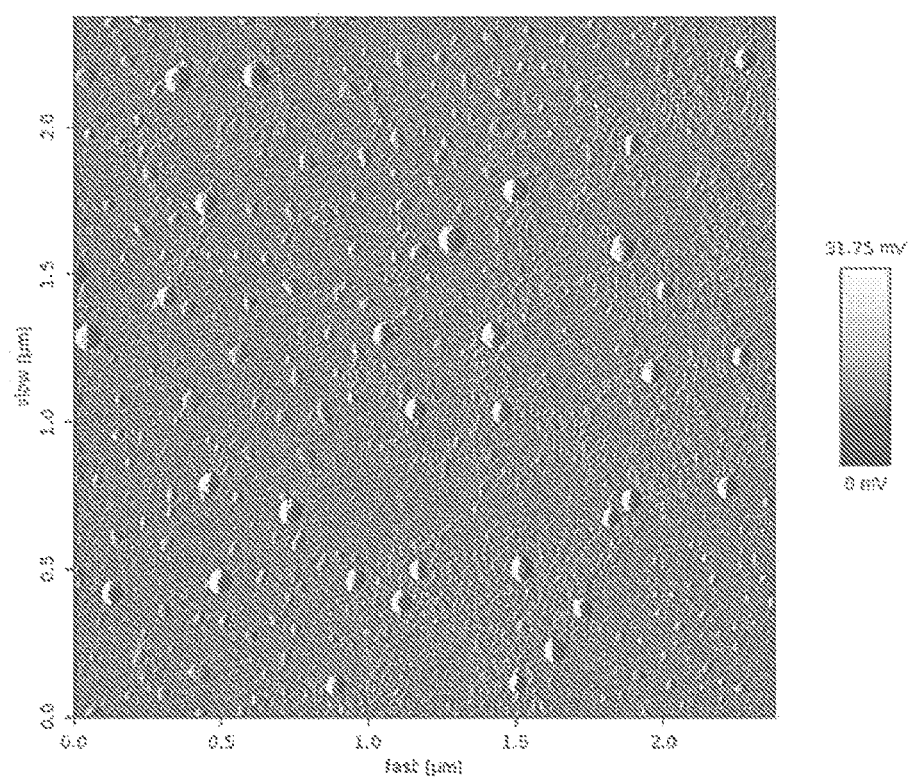
FIG. 2A: an atomic force microscopy pictogram of surface characterization of exemplary liposomes (comprised of: a lipid phase comprising DLinDMA/Chol/DSPC/DMG-PEG/PE-PEG-Amine (mol/mol 40:40:18:1.5:0.5) and coated with 7 KDa HA)

Dynamic light scattering for characterization of the particles was performed to identify Surface characterization of the particles. Surface characterization was done for the first formulation of Table 1, that comprises DLinDMA/Chol/DSPC/DMG-PEG/PE-PEG-Amine (mol/mol 40:40:18:1.5:0.5)—coated with 7 KDa HA. A pictogram of the particles, obtained from Atomic force microscopy is shown in FIG. 2A. The results show shows disperse, round shape particles with Young Modulus of 43.1 MPa.

In contrast, similar formulations that did not include PEG-Amine in the formulation, but rather PE (ranging from 20% mole, 10%, 5%, 2%, 1% or 0.5%) could not form particles as determined by visual inspection: which only shows aggregate that sediment. Further, a typical dynamic light scattering size distribution could not be obtained because of high noise to signal ratio, indicating the there are no particles stable enough with such formulations.

Figure 2B:
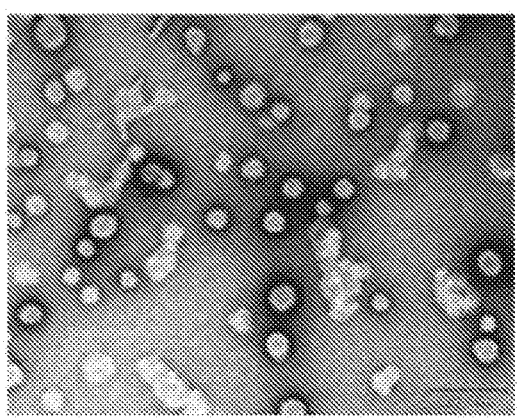
FIG. 2B and FIG. 2D show pictograms of TEM analysis of the DLinMC3-DMA/DSPC/Chol/DMG-PEG/DCPE-PEG-Amine (mol/mol 50:10:38:18:1.5:0.5) and DLinMC3-DMA/DSPC/Chol/DMG-PEG/DCPE-PEG-Amine (mol/mol 50:10:38:18:1.5:0.5)-HA (5 KDa MW), respectively.
Figure 2D:
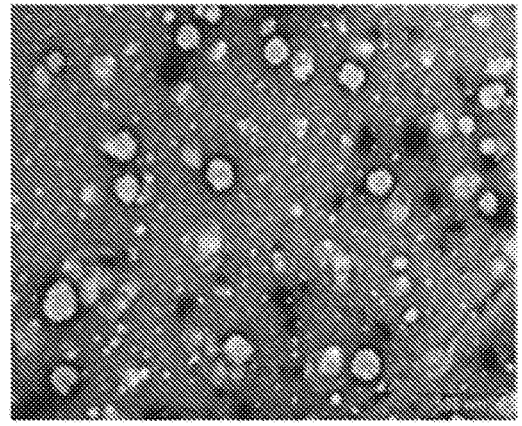
Figure 2C:
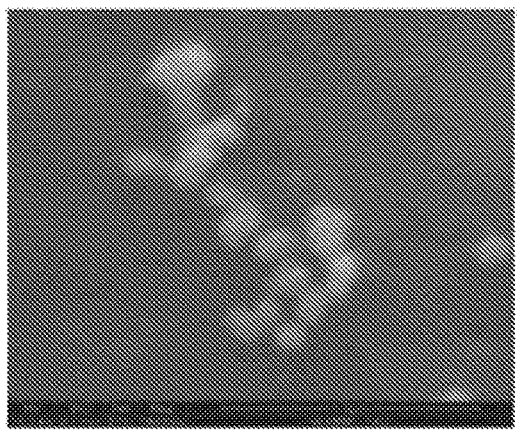
FIG. 2C and FIG. 2E show pictograms of SEM analysis of the DLinMC3-DMA/DSPC/Chol/DMG-PEG/DCPE-PEG-Amine (mol/mol 50:10:38:18:1.5:0.5) and DLinMC3-DMA/DSPC/Chol/DMG-PEG/DCPE-PEG-Amine (mol/mol 50:10:38:18:1.5:0.5)-HA (5 KDa MW), respectively. Bar scale-1 μm.
Figure 2E:
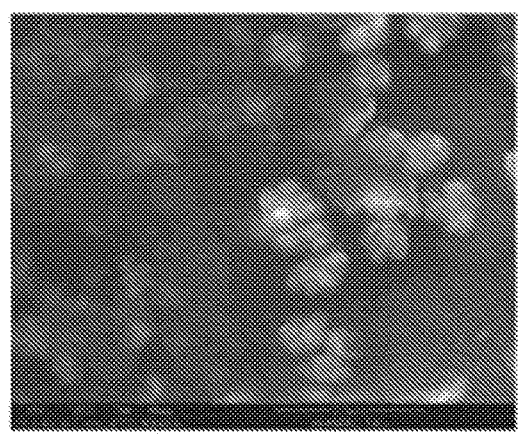

Analysis of exemplary formulations which include DLinMC3-DMA/DSPC/Chol/DMG-PEG/DCPE-PEG-Amine (mol/mol 50:10:38:18:1.5:0.5) alone or conjugated to HA (5 Kda MW), are shown in FIGS. 2B-E. FIGS. 2B and 2D show pictograms of TEM analysis of the DLinMC3-DMA/DSPC/Chol/DMG-PEG/DCPE-PEG-Amine (mol/mol 50:10:38:18:1.5:0.5) and DLinMC3-DMA/DSPC/Chol/DMG-PEG/DCPE-PEG-Amine (mol/mol 50:10:38:18:1.5:0.5)-HA (5 KDa MW), respectively. FIGS. 2C and 2E show pictograms of SEM analysis of the DLinMC3-DMA/DSPC/Chol/DMG-PEG/DCPE-PEG-Amine (mol/mol 50:10:38:18:1.5:0.5) and DLinMC3-DMA/DSPC/Chol/DMG-PEG/DCPE-PEG-Amine (mol/mol 50:10:38:18:1.5:0.5)-HA (5 KDa MW), respectively. The zeta potential of the formulations were 3.8±1 without conjugated HA and —8.2±0.7 after conjugation to HA. As shown in FIGS. 2 B-E, the particles without the HA conjugated thereto have globular shapes and round surfaces whereas the particles with the HA exhibit a flower-like shape on the particles.

All together, the results indicate that the inclusion of PEG-Amine in the formulation enables the formation of stable, evenly distributed particles. The results further suggest that inclusion of additional PEG derivatives further improves the condensation and stability of the liposomes. The results further demonstrate that the presence of the nucleic acid in the liposome enables the formation of the particles.

Example 3

Efficient Knockdown of Target Gene by siRNA Encapsulated within the Liposomes in Target Cells Harboring CD44

Material and methods:

Cell Lines:

Human lung adenocarcinoma cells (A549) expressing CD44 and human prostate cancer (LnCap) cells lacking CD44 (by flow cytometry) were purchased from American Type Culture Collection (ATCC). Cells were grown in RPMI-1640 supplemented with 15% FBS and 1% antibiotics as recommended by ATCC.

siRNA molecules: PLK1 siRNA molecules were synthesized according to the following published sequence: 5'-UmGmAAGAAGAUCmAmCCmCUCCUUmA-3' (Sense) (SEQ ID NO: 1). To enhance siRNA stability, the sense and antisense strands were modified by 2'-O-methylation (m).

Luciferase siRNA molecules (siLuci): Sense strand: 5' cuuAcGcuGAGuAcuucGAdTsdT (SEQ ID NO: 6)' Anti-Sense strand: 5' UCGAAGuACUcAGCGuAAGdTsdT (SEQ ID NO: 7).

2'-OMe modified nucleotides are in lower case, and phosphorothioate linkages are represented by "s".

Transfection in human A549 and LnCap cells: Cells were grown in RPMI-1640 with 15% FBS and 1% antibiotics at 37° C. Cells were plated in polystyrene coated 12-well plate with a density of $7 \times 10^4$ cells/well on the day of transfection. Different formulations of the lipid phase and/or free (naked) siRNA at 0.37 μM concentration in complete medium were added and incubated for 48 h or 72 h. Total RNA was isolated after 24 h and 48 h and PCR was performed to calculate the amount of PLK1 transcript present in cancer cells after transfection.

Quantitative real time PCR analysis: Total RNA was isolated using EZ-RNA Kit (Biological Industries) after 24 h or 48 h of incubation with different nanoparticle formulations and naked siRNA, according to the manufacturer's protocol. The mRNA was transcribed into cDNA using the High-Capacity cDNA Reverse Transcription Kits (SWIFT-Max Pro, ESCO). Thereafter, 0.625 ng of cDNA was subjected to quantitative real-time PCR analyses targeting Plk1 and GAPDH (as the house keeping gene). Primer sequences were: Plk1 forward 5'-ACCAGCACGTCGTAGGATTC-3' (SEQ ID NO:2), Plk1 reverse 5'-CAAGCACAATTGCCG-TAGG-3' (SEQ ID NO:3). GAPDH Forward 5'-TCA-GGGTTTCACATTTGGCA (SEQ ID NO:4), GAPDH reverse 5'-GAGCAT GGATCGGAAAACCA (SEQ ID NO:8). Syber green was used to detect PCR products. Analysis was performed using the StepOne Real-Time PCR System and the StepOne v2.0 software (Applied Biosystems). Relative gene expression values were determined by the ΔΔCT method using the StepOne v2.0 software (Applied Biosystems). Data are presented as the fold difference in Plk1 expression normalized to the housekeeping gene GAPDH as endogenous reference and relative to the untreated control cells.

Cell viability assay: In vitro cell viability was measured by XTT assay. XTT reagent (Biological Industries) was added to the cells 48 h after treatment with the liposomal formulations and incubated for 4 h according to manufacturer protocol. Absorbance was measured at 450-500 nm wave length by micro plate reader (BioTEk, Israel).

Particle size measurement: The sizes of the liposomes were measured in PBS by dynamic light scattering using Zetasizer Nano (Malvern, UK).

In order to test the in-vitro effect of the liposomes in reducing expression of a target gene in a target cell (harboring CD44), human lung adenocarcinoma cell line A549 expressing high amounts of CD44 and the non-CD44-expressing cells LNCAP (human prostate cancer) as specificity control, were used.

Statistical Analysis

Differences between two means were tested using an unpaired, two-sided Student's t-test. Differences between treatment groups were evaluated by one-way ANOVA test of SPSS software. Kaplan-Meier survival analysis was preformed with a GraphPad Prism version 5.0b.

Figure 3:
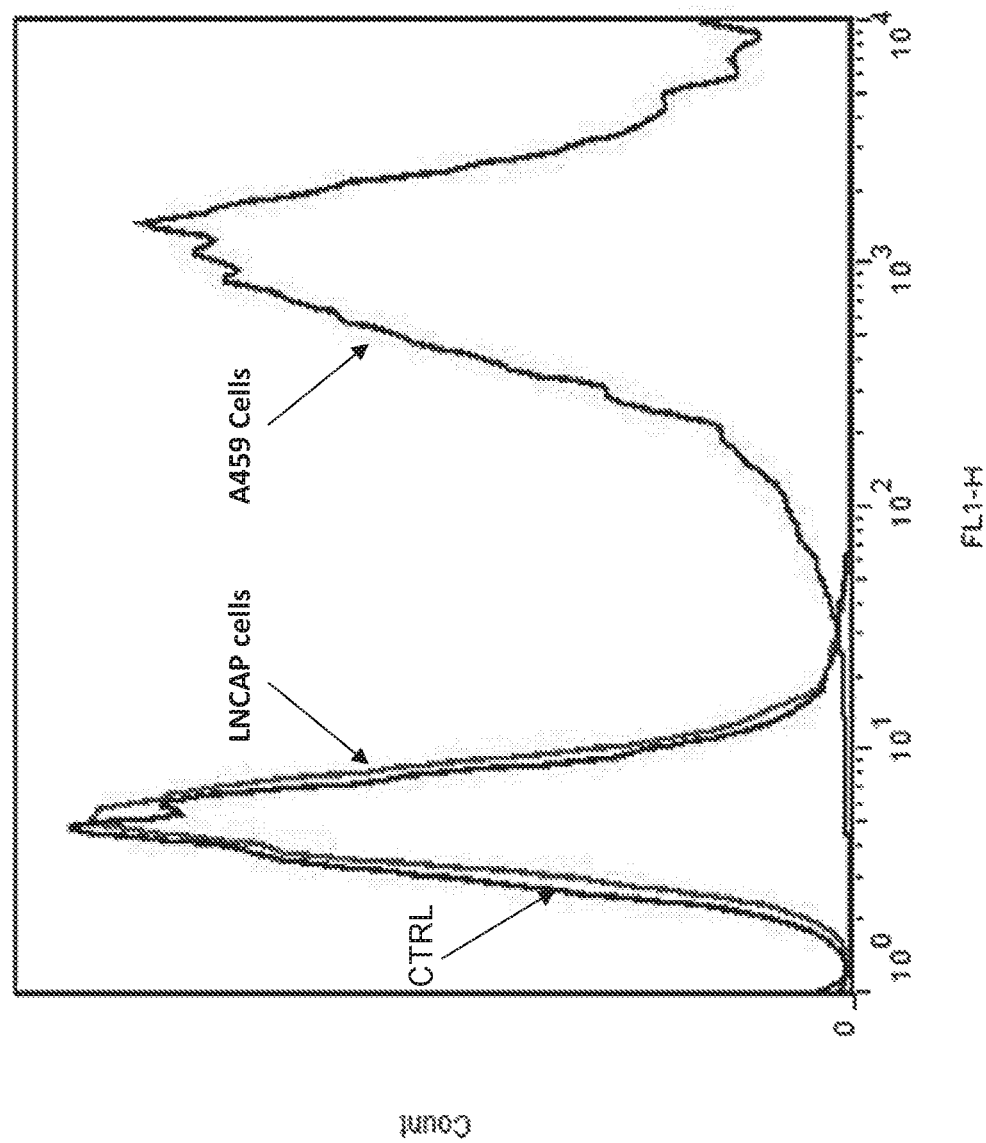
FIG. 3: FACS scan analysis of expression of CD44 in A459 cells and LnCap cells, stained with pan-CD44 monoclonal antibody (clone IM7) or its isotype control mAb (Rat IgG2b). Ten thousand cells, analyzed at each experimental point. Data analysis was performed using FlowJo software (Tree Star, Inc. Oregon, USA). Arrows indicate A549 cells, LnCap cells and CTRL (isotype control staining).

CD44 was surface labeled with a pan-CD44 monoclonal antibody (clone IM7) or its isotype control mAb (Rat IgG2b) as previously reported (Landesman-Milo D. et al., Cancer Letters 2012). Samples were collected and analyzed using a FACSscan CellQuest (Becton Dickinson, Franklin Lakes, N.J.).). Ten thousand cells were analyzed at each experimental point. Data analysis was performed using FlowJo software (Tree Star, Inc. Oregon, USA). FIG. 3 shows representative CD44 expression in the tested cells (A549 cells, LnCap cells and CTRL (isotype control staining).

Next, the cells were transfected with the following lipid-based compositions (formulations) (Table 2):

TABLE 2

| No. | Formulation (composition of the liposome) |
|---|---|
| 1 | DLinDMA/Chol/DSPC/DMG-PEG/PE-PEG-Amine (mol/mol 40:40:18:1.5:0.5) |
| 2 | DLinDMA/Chol/DSPC/DMG-PEG/PE-PEG-Amine (mol/mol 40:40:18:1.5:0.5) - coated with 7 KDa HA |
| 3 | DLinDMA/Chol/DSPC/DMG-PEG/PE-PEG-Amine (mol/mol 40:40:18:1.5:0.5) - coated with 800 KDa HA |

TABLE 2-continued

| No. | Formulation (composition of the liposome) |
|---|---|
| 4 | DLin-KC2-DMA/Chol/DSPC/DMG-PEG/PE-PEG-Amine (mol/mol 40:40:18:1.5:0.5) |
| 5 | DLin-KC2-DMA/Chol/DSPC/DMG-PEG/PE-PEG-Amine (mol/mol 40:40:18:1.5:0.5)- HA (7 KDa) |
| 6 | DLin-KC2-DMA/Chol/DSPC/DMG-PEG/PE-PEG-Amine (mol/mol 40:40:18:1.5:0.5)- HA (800 KDa) |

Figure 4A:
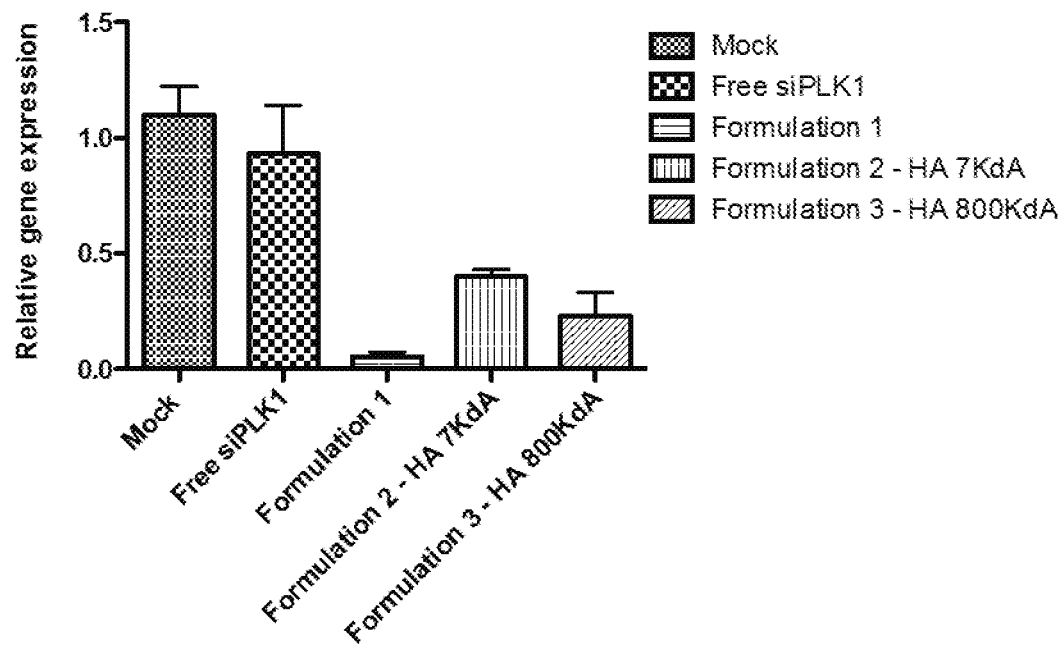
FIGS. 4A-B: Bar graphs showing the relative gene expression of PLK1 in A549 cells (CD44+ cells), transfected with formulations 1-3 (FIG. 4A) and 4-6 (FIG. 4B), respectively. Formulations 1-6 are detailed in Table 2, below. Mock=transfection without nucleic acid. siPLK1=transfection with naked siRNA molecule.
Figure 4B:
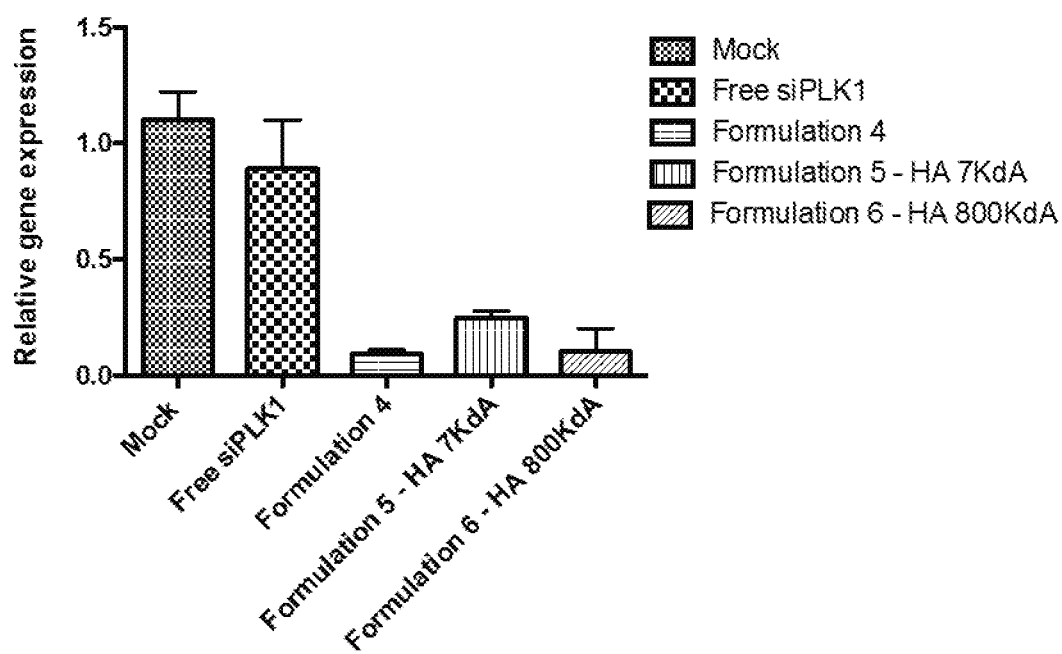

The results presented in FIGS. 4A-B, show the relative gene expression of PLK1 in A549 cells, transfected with formulations 1-3 and 4-6, respectively.

Figure 4C:
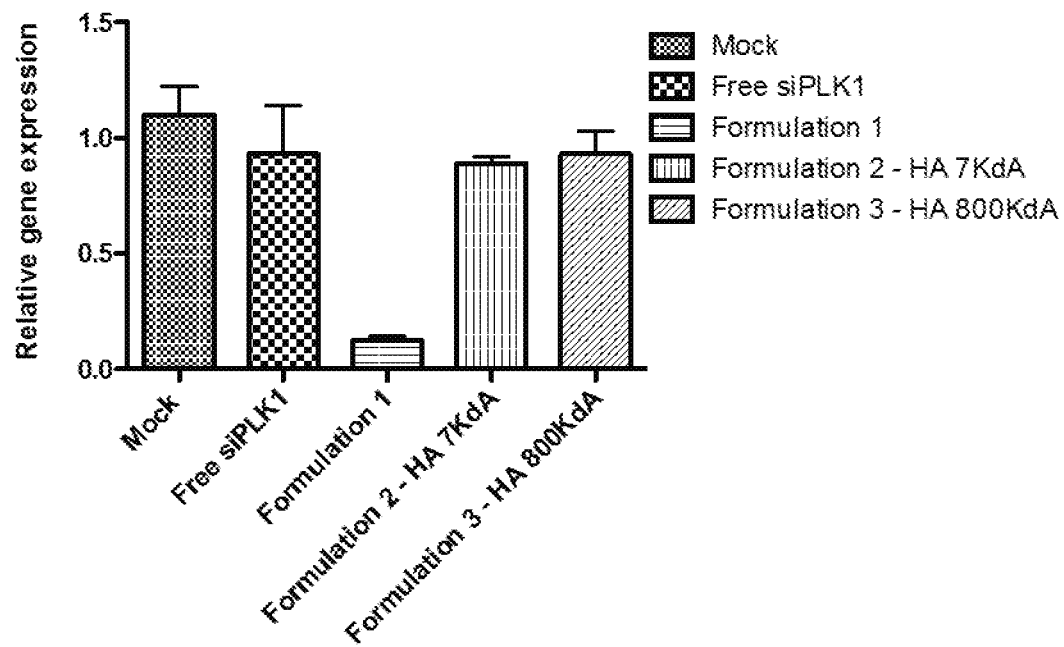
FIGS. 4C-D: Bar graphs showing the relative gene expression of PLK1 in LnCap cells (CD44− cells), transfected with formulations 1-3 (FIG. 4C) and 4-6 (FIG. 4D), respectively. Formulations 1-6 are detailed in Table 2, below. Mock=transfection without nucleic acid. siPLK1=transfection with naked siRNA molecule.
Figure 4D:
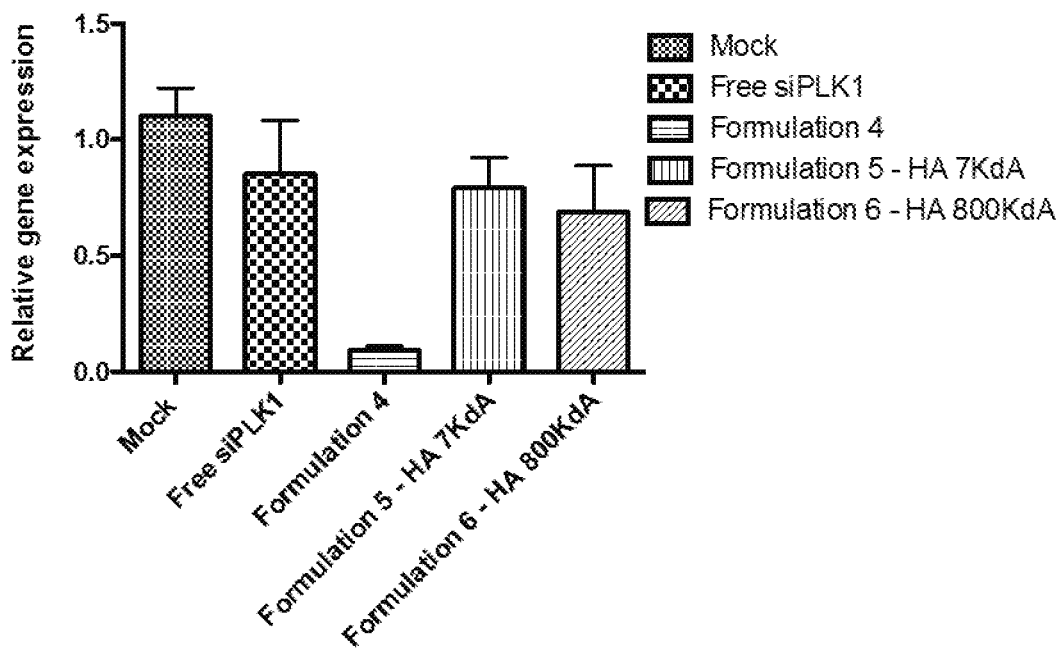

The results presented in FIGS. 4C-D, show the relative gene expression of PLK1 in LnCap cells, transfected with formulations 1-3 and 4-6, respectively.

The results show that the HA coating provides the liposomes targeting capabilities, as formulations which have an HA coating on the surface of the particles are specifically directed to target cells harboring CD44, but not to cells, which do no carry the CD44 receptor. The results further demonstrate that the tested formulations indeed capable of efficiently delivering siRNA to the target cell, whereby the siRNA is able to exert a biological effect by reducing expression of a target gene. In addition, the results show that HA having higher molecular weight (800 KDa) provides enhanced effect on target cells as compared to low molecular weight (7 KDa) HA.

Example 4

Specific Knockdown of a Target Gene Expression in A549 Human Xenograft Model Upon Single i.v. Injection A549 cells (human lung adenocarcinoma cells (at $3 \times 10^6$ cells) were implanted above the femoral joint in nude mice (Nu/Nu), upon three washing with HBSS (biological industries, Israel) to establish A459 tumor model.

The mice were then intravenously injected with various particle compositions and 96 hours post the single i.v. injection, the effect on gene expression of the target gene (Cyclin D1) was assayed.

Cyclin D1-siRNA at a concentration of 2 mg/Kg was formulated in the MC3-PEG-Amine—HA (High Mw 800 kDa) and i.v. administrated to the mice.

siRNA sequences against the cyclin D1 (CCND1) gene NM_053056 (siD1, sense strand: GUAGGACUCU-CAUUCGGGATT (SEQ ID NO: 5)) were designed and screened by Alnylam Pharmaceuticals (Cambridge Mass., USA) and previously published (See Weinstein S. et al. PLOS ONE, 2012). Control genes to which the expression of the Cyclin D1 target gene was normalized to were U6, eIF3a and eIF3c.

Figure 5:
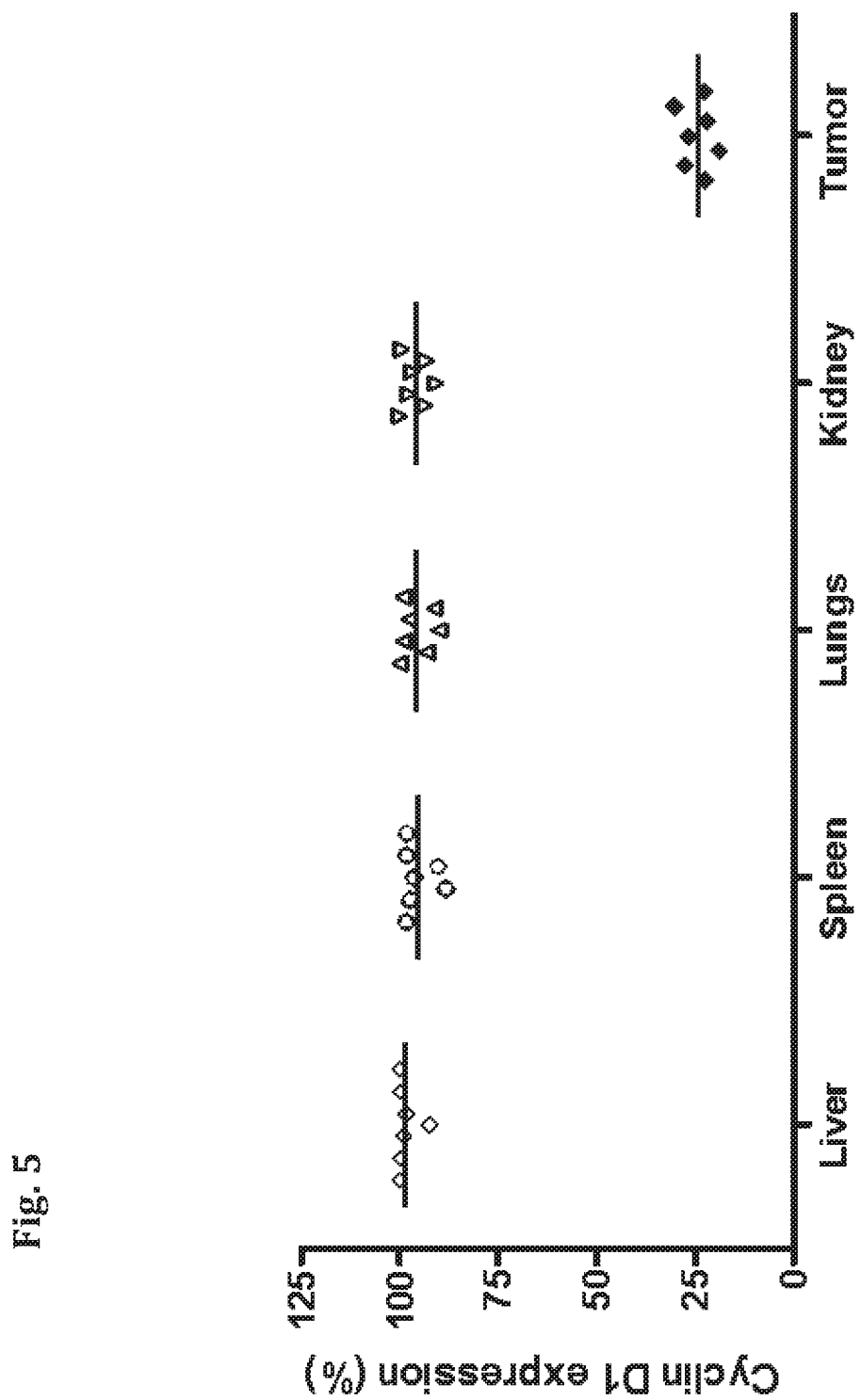
FIG. 5: A graph showing relative expression of Cyclin D1 in various tissues obtained from seven model mice (injected with A459 cells, as detailed below), 96 hours after i.v. administration of the cationic liposomes of the present invention (comprising a specific siRNA directed against Cyclin D1). The expression of the Cyclin D1 target gene was normalized to the expression of U6, eIF3a and eIF3c control genes.

The Intravenous injected particle composition was done in saline, supplemented with 5% glucose at day 0, 3 and 6 at 100 μL volume. Bodyweight was monitored every 2 days. The results are presented in FIG. 5, which shows the relative expression of Cyclin D1 in various tissues of the mice, 96 hours after administration of the particles. The results demonstrate a specific reduction in expression of the Cyclin D1 in the tumor, but not in the lungs, spleen or kidneys, 96 hours post injection. About 75% reduction in expression of Cyclin D1 can be observed 96 hours post the last i.v. injection in the tumor. The results demonstrate the specificity of the particles to tumors, but not to other, non tumor cells. The results further show the efficiency of the particles in the in-vivo delivery of a functional nucleic acid to a target cell, which can effectively affect the expression of target gene in a target cell.

Example 5

Specific Interaction of Liposomal Particles Conjugated to HA with Glioblastoma (GBM) Cells Materials and Methods:

Cell lines: human glioblastoma cell lines, T98G, U251 and U87MG (WHO grade IV) were used as model cells for GBM. The selected cell lines represent a spectrum of different genetic lesions. All cell lines were grown in monolayer and maintained in high-glucose (4.5 g/L) Dulbecco's modified Eagles's medium (DMEM) supplemented with 10% fetal bovine serum (FBS), 1% penicillin/streptomycin, and 2 mML-glutamine (Biological Industries). Cells were incubated at 37° C. with 5% CO2 and were subcultured twice weekly.

Flow cytometry analysis and Immunohistochemistry: Flow cytometry of cell surface CD44 antigens was performed as described by Coehn et. al. (2014). Briefly, Alexa Fluor 488-conjugated rat anti-human CD44 (clone 1M7) from Biolegend (San Diego, Calif., USA) or IgG2b isotype control were incubated with 0.5 $10^6$ GBM cells (0.25 ug per $10^6$ cells) on ice for 30 min followed by washing with PBS. Data was acquired using FACSCalibur with CellQuest software (Becton Dickinson, Franklin Lakes, N.J., USA). Data analysis was performed using the FlowJo software (Tree Star, Inc., Oregon, USA).

Eight paraffin blocks of GBM patients and a single Gliosarcoma block were identified by examination of hematoxylin and eosin stained slides. From each tumor block, 4 μm thick sections were cut onto positive charged slides and used for IHC. The slides were warmed up to 60° C. for 1 hour and after that processed to a fully automated protocol (Benchmark XT, Ventana medical system, Inc., Tucson, Ariz., USA) and the related Ventana reagents were used, using standard manufacturer's instructions. Briefly, after sections were dewaxed and rehydrated, a CC1 standard Benchmark XT pretreatment (60 min) for antigen retrieval was selected (Ventana Medical Systems). Sections were then incubated 40 min with a prediluted mouse anti-human CD44 (08-0184 from Zymed, San Francisco, Calif., USA). Detection was performed with ultraView detection kit (Ventana Medical Systems) and counterstained with hematoxylin (4 min) (Ventana Medical Systems). After the run on the autostainer was completed, slides were dehydrated in 70% ethanol, 95% ethanol and 100% ethanol for 10 second each ethanol. Before coverslipping, sections were cleared in xylene for 10 seconds and mount with Entellan. Analysis score was based on CD44 scattering within the tumor site. This staining is semiquantitatively scored; +(positive), ++(strongly positive), or +++(very strongly positive).

Figure 6A:
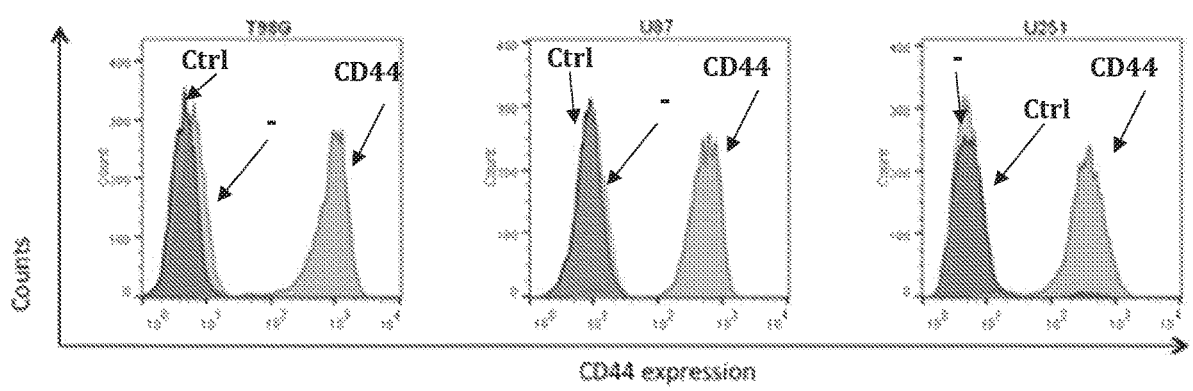
FIGS. 6A-B—Expression of CD44 in GBM cells.
Figure 6B:
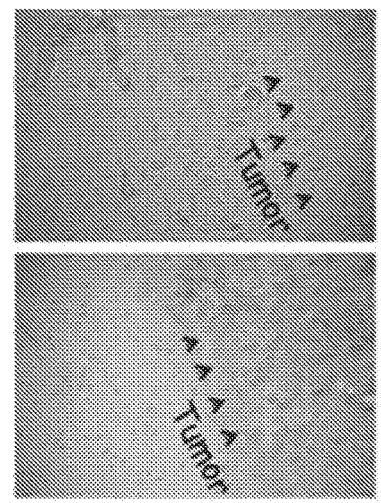

The expression of CD44 in various human GBM cell lines and primary human glioma samples (obtained from GBM patients) was tested. To this aim, three representative GBM cell lines were used: T98G, U87MG and U251 (all have been reported to be resistant to chemotherapy treatment). Pan anti-CD44 mAb (monoclonal antibody) was used to detect the expression of CD44 in all three-cell lines and, as shown in the FACS analysis presented in FIG. 6A, all cells lines were shown to have a high CD44 expression. Next, the expression of CD44 in primary glioma cells excreted from human patients was tested using immunohistochemistry. Representative staining pictograms are shown in the right hand panel of FIG. 6B. Further shown in FIG. 6B is a list of patient's samples with semi-quantitative analysis of CD44 expression.

Next, the liposomal particles (comprising Dlin-MC3-DMA, DSPC, Chol, DMG-PEG and DSPE-PEG amine at 50:10:38:1.5:0.5 mole ratio, total lipid concentration 9.64 mM)) were tested for their binding ability to glioma cells. The particles entrapped a Cy5-siRNA (1:16 w/w siRNA to lipid) as a control marker (whereby identification thereof in the target cells is indicative of association of the particles and the cells). The results presented in FIGS. 7A-B demonstrate that particles comprising HA (HA-LP (HA-lipid based particles)) can interact/bind U87GM cells (FIG. 7A) as well as primary GBM cells form GBM patients (FIG. 7B), whereas particles that do not include the HA (LP (lipid particles)).

Example 6

Induction of Cell Death in Glioblastoma (GBM) Cells Lines Using the HA-Liposomal Particles Glioblastoma cells are known to be resistant to chemotherapy. To verify the resistance of U87MG cells to chemotherapy, two classical chemotherapeutic agents (namely, doxorubicin (DOX) and 1,3-bis(2-chloroethyl)-1-nitrosourea (BCNU)) were tested for their effect on the cells.

Briefly, U87MG cells were seeded onto 96 multi-well plates ($1 \times 10^4$ cells/well) in 200 ul culture medium. Twenty-four hours later, the medium was replaced by treatment medium, which contained different concentrations of DOX (Teva pharmaceutical, Israel) and BCNU (MW 214, purchased from Calbiochem (San Diego, Calif.)) for 48 h followed by an extensive wash with PBS and a standard XTT survival assay.

The results presented in FIG. 8 demonstrate that even at the highest dose of 100 μM under static culturing conditions for 48 h, cell survival was >50%, thereby confirming their intrinsic resistance to chemotherapy.

In order to overcome/by pass the resistance mechanism of the cells, which involved extrsion of large molecules from the cells by eflux pumps, a specific cell cycle inhibitor, for exmaple, in the form of a nucleic acid, such as, siRNA may be used.

To this aim, specific siRNA molecules (siPLK1) directed against Polo-like Kinase 1(PLK1), which is a serine-threonine protine kinase involved in cell cycle regulation, a or control siRNA (siLuciferase; siLuci) were entraped in the HA-LP or in the control particles (LP) lacking the targeting ligand. The experiment was performed under shear flow conditions as described by Shulman et. al. (2009), in order to simulate the cerebrospinal fluid (CSF) flow for 10 minuntes (min), followed by incubation in static condition with fresh media. 72 h post transfection, cells were analyzed for mRNA levels of PLK1. Briefly, The mRNA levels of polo-like kinase 1 (PLK1 gene) in the cells was quantified by real-time PCR. 72 h post transfection (10 min under shear flow and additional 72 h under static conditions with full freash media). Total RNA was isolated using the EzRNA RNA purification kit (Biological industries, Beit Haemek, Israel), and 1 μg of RNA from each sample was reverse transcribed into cDNA using the High Capacity cDNA Reverse Transcription Kit (Applied Biosystems, Foster City, Calif.), Quantification of cDNA (5 ng total) was performed on the step one Sequence Detection System (Applied Biosystems, Foster City, Calif.), using syber green (Applied Biosystems). GAPDH was chosen as a house keeping gene. Primer sequences are as detailed in Example 3.

Figure 9A:
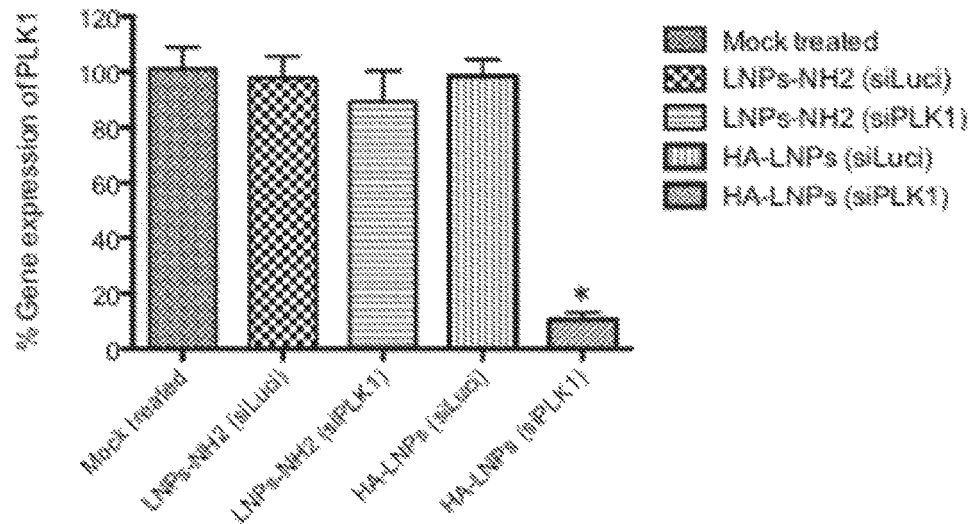
FIGS. 9A-C PLK1 induce specific cell death in Glioma cells.
Figure 9B:
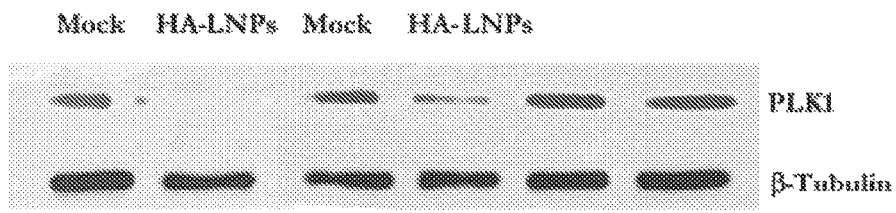
Figure 9C:
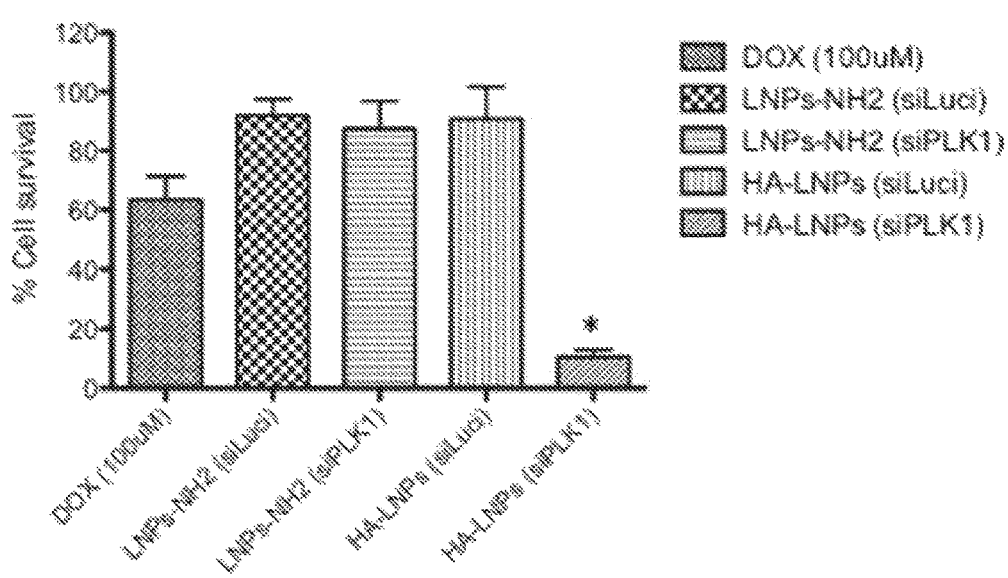

The results presesnted in FIGS. 9A-B demosntrate that HA-coated particles induced a robust gene silencing under shear flow both at the mRNA and PLK1 protein level (FIGS. 9A and 9B, respectively). PLK1 protein was silenced for 96 h and recovery of the protein level was observed at 144 h post transfection (FIG. 9B). This silencing effect was specific since HA-coated LNPs netraping a control siRNA (siLuci) did not reduce the expression of PLK1 mRNA in the cells. In addition, the robust silencing observed with siPLK1 delivered via HA-LNPs was translated to effective cell death (FIG. 9C). The control particles (LP), which do not include HA, did not reduce mRNA levels of PLK1 when siPLK1 or siLuci were entrapped therein, nor did they induce cell death. The results suggest that the HA coating on the LNPs surface bind with high affinity to CD44 expressed on the GBM cells, even under shear flow and that the internalization process is fast and efficient.

Example 7

In-Vivo Delivery of Nucleic Acid into a Glioma Established Model

Material and Methods:

U87MG Orthotopic GBM Model Establishment: Cells were maintained in Dulbecco's modified Eagle's medium supplemented with 10% bovine serum and incubated at 37° C. in a humidified atmosphere containing 5% carbon dioxide/95% air. On the day of implantation, monolayer cell cultures were harvested using a 0.05% trypsin/ethylene ediamine tetra acetic acid solution. Cells were counted, resuspended in 3 μl of PBS. $5 \times 10^5$ U87MG cells were injected into each animal in a 3 μL volume.

Animal Hosts 4-to-6-week-old female nude mice (strain nu/nu), each weighing ~20 g, were used for this study. All procedures were performed in accordance with regulations of the Animal Care and Use Committee of the Sheba Medical Center. The mice were housed in groups of five in cages within a standardized barrier facility and maintained on a 12-hour day/night cycle at 23° C. Animals were given free access to laboratory chow and water. All instruments were sterilized before the procedure and sterile small-animal surgical techniques were used. The mice were allowed to feed until the time of surgery. Animals were anesthetized by intraperitoneal injection of ketamine/xylazine solution (200 mg ketamine and 20 mg xylazine in 17 ml of saline) at a dosage of 0.15 mg/10 g body weight.

Identification of Implantation Site. The animal's head was stabilized manually by holding it with one finger behind the interaural line. The skin was prepared with povidone iodine solution and then a 2- to 3-mm-long incision was made just to the right of midline and anterior to the interaural line so that the coronal and sagittal sutures can be identified; the bregma is located. The entry site was marked at a point 2.5 mm lateral and 1 mm anterior to the bregma. This point is chosen because it is located directly above the caudate nucleus, which has been shown to be a highly reliable intracranial site for tumor engraftment.

Drill Hole Placement. Using a small hand-controlled twist drill that is 1 mm in diameter a drill hole was made in the animal's skull at the entry point. The drill bit penetrates the dura and thereby opens it.

Cell Injection with Hamilton Syringe. The 3-μl cell suspension was drawn up into the cuffed of the 26-gauge needle of a Hamilton syringe. Using a stereotactic apparatus the needle of the Hamilton syringe was slowly lowered into the central skull hole made by the twist drill. Based on the entry point and the depth of needle penetration, it is certain that the cells are injected into the caudate nucleus. The cell suspension was slowly injected (typically over 5 minutes) into the mouse's brain. After the entire volume of the cell suspension was injected, the needle was manually removed. A suture was placed to close the scalp. The mice were kept warm until they recover from anesthesia and were allowed to move around freely until the time of intratumoral injection of the therapeutic interventions. In the interim the injected tumor cells proliferate and establish themselves as intraparenchymal xenografts. The technique of intratumoral injection mimics the technique of tumor cell implantation, except that HA-LNPs were delivered into the established xenograft in 4 doses of 3 μL each. The first doses were given at days 7 and 9 and the next disease were given at days 20 and 22. Mice were monitored for global toxicity changes including changes in bodyweight that were not observed for the entire period of the experiment.

Figure 10:
FIG. 10—show pictogram of representative histological analysis using H&E staining on an orthotopic GBM model, to evaluate tumor size and location 12 days post tumor inoculation by stereotactic implantation of U87GM cells.

As detailed above, Human U87G cells were used to generate an orthotopic xenograft model in athymic BALA/c nu/nu mice. This serves as a model for studying the growth, biology, and treatment of human gliomas. A suspension of 3 ul of $5 \times 10^5$ U87G cells was injected into each animal. Histological analysis was performed at day 12 (post inoculation). A representative histology pictogram is presented in FIG. 10.

Figure 11A:
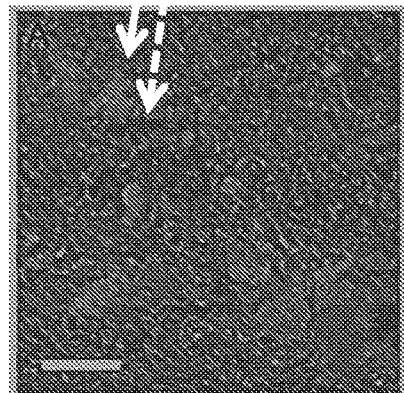
FIGS. 11A-C—show representative confocal microscopy pictograms of histological sections after administration (by injection) of liposomal particles comprising HA and encompassing Cy3-siRNA into tumor site. At different time points after administration.
Figure 11B:
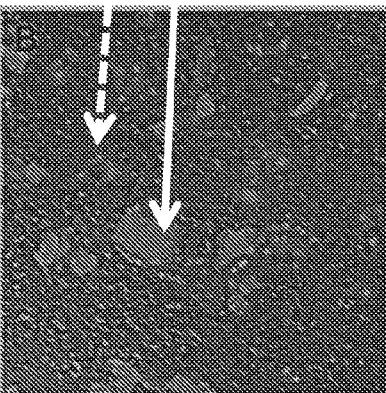
Figure 11C:
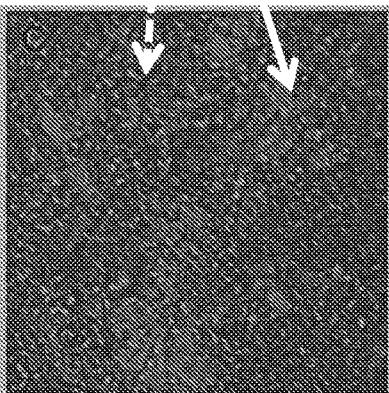

Next, 3 μL of 0.2 mg/Kg body Cy3-siRNAs encasulated within the particles (HA-LP) or via LP) were administered (injection) directly into the tumor vicinity at day 20 after tumor inoculation. The mice (n=6) were sacrificed at 3 hours, 6 hours and 24 hours (h) post administration. Brains were sectioned and immediately taken into confocal microscopy analysis to identify the distribution of the Cy3-siRNAs within the tumor at different time points. Representative data of the results after administration of the HA-LP particles are presented in the pictograms shown in FIGS. 11A-C. Detection of Cy3 signal was observed only in HA-LP treated mice in all sections and increased with time from 3, 6 to 24 h post administration (FIG. 11A, FIG. 11B and FIG. 11C, respectively). When administered with LP (i.e. particles without HA), no Cy3 signal was detected in the tumor tissue. This may be attributed to the shear flow by the cerebral spinal fluid (CSF) which may cause such particles not to adhere to the U87MG cells, wherase particles comprising HA, adhere to the cells due to the specific bininidg of HA to the CD44 expressed on the cells.

Example 8

In-Vivo Silencing of PLK1 in U87MG Cells Prolongs the Survival of GBM-Bearing Mice Materials and Methods:

Preparaton of Single Cell Suspension from Brain Tissue: Neural tissues were dissociated to single-cell suspension by enzymatic degradation using the GentleMACS Dissociator and neural tissue dissociation kit (Miltenyi Biotech), according to the manufacturer protocol. Briefly, mice were perfused with either HBSS or PBS and brains were removed and weighed in order to adjust the buffers and enzyme mix to the amount of tissue. A pre-warmed enzyme mix was added to the tissue and incubated with agitation at 37° C.

The tissue was mechanically dissociated and the suspension was applied to a 70 µm strainer. Myelin was removed using Myelin Removal Beads II (Miltenyi Biotech) as it can interfere with flow cytometric analysis. Cells were processed immediately and stained with anti-human CD44v6-FITC (non-cross reactive with mice, clone MCA1730F, Bio-Rad) in order to identify the U87MG cells. Cells were incubated on ice for 30 min, then washed twice and subjected to FACS sorting using FACSAria III (BD). Sorted cells were moved directly into EzRNA RNA purification kit (Biological industries, Beit Haemek, Israel) and analyzed for PLK1 mRNA levels using QPCR as detailed above.

Figure 12A:
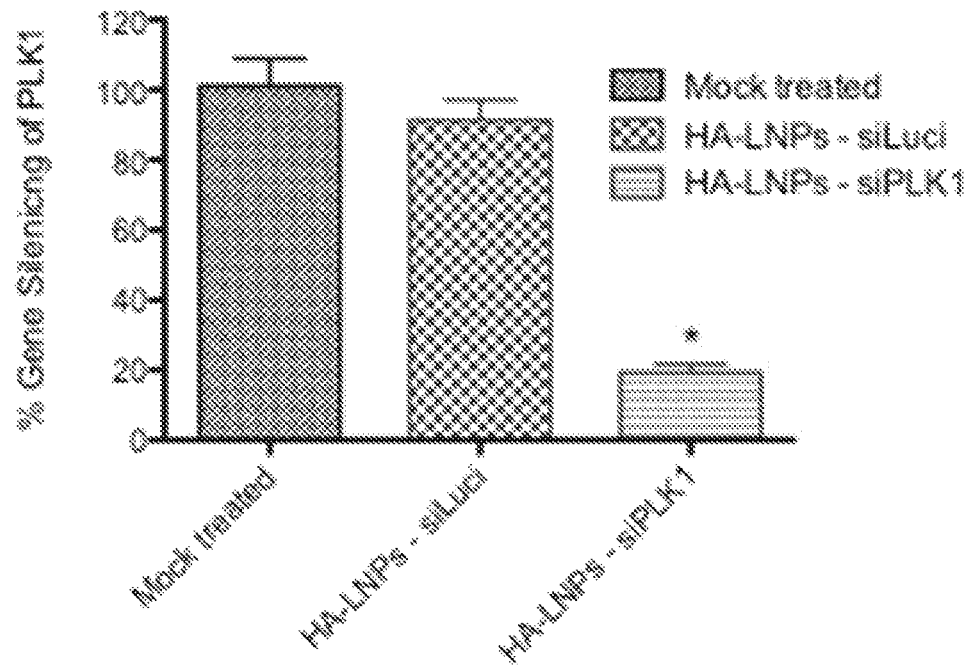
FIGS. 12A-D—Graphs showing the in-vivo effect of silencing of a target gene (PLK1) on GBM cells and survival of GBM-bearing mice.

The GBM orthotopic model was further used to test the in vivo silencing of PLK1 gene expression upon local administration (0.5 mg/Kg body) of the particles encapsulating siRNA against PLK1 (as in example 6), at day 20 and 22 of tumor inoculation. In order to identify the tumor cells from other types of cells in the brain, tumor tissue was taken out, a single cell suspension was made and the cells were incubated with a surface marker expressed on U87MG cells (CD44v6). An anti-human CD44v6-FITC antibody (non-cross reactive with mice) was incubated on ice for 30 min, then washed twice and subjected to FACS sorting. FACS (FACSAria III, BD) sorted cells were analyzed for PLK1 mRNA levels using QPCR. As shown in the bar graphs of FIG. 12A, a robust knockdown of 80% was observed in U87MG CD44v6$^+$ cells treated with siPLK1 that was delivered with the HA-LP ("HA-LNPs"). No effect on PLK1 expression was observed when control siRNA (siLuci) was used.

Figure 12B:
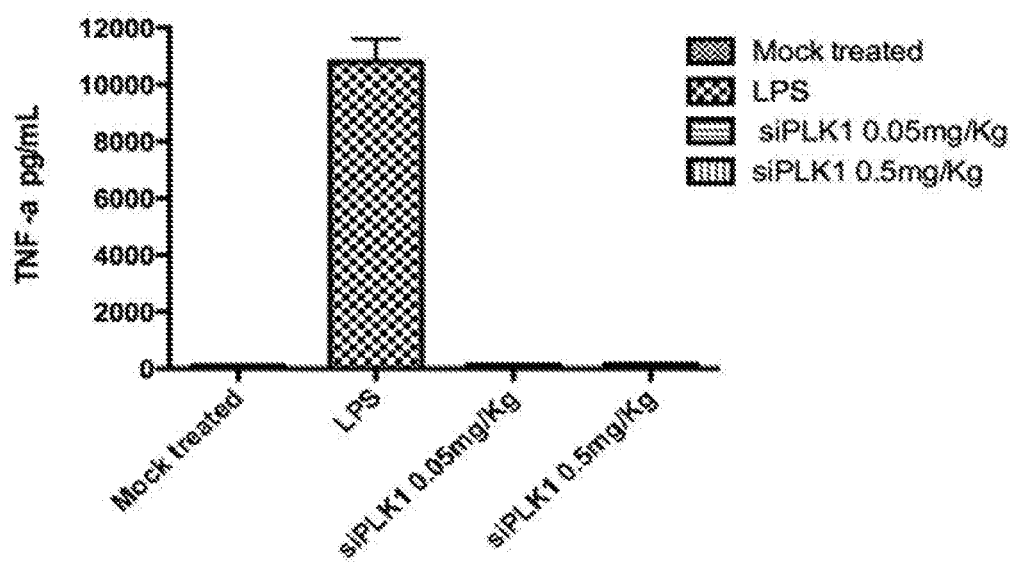
Figure 12C:
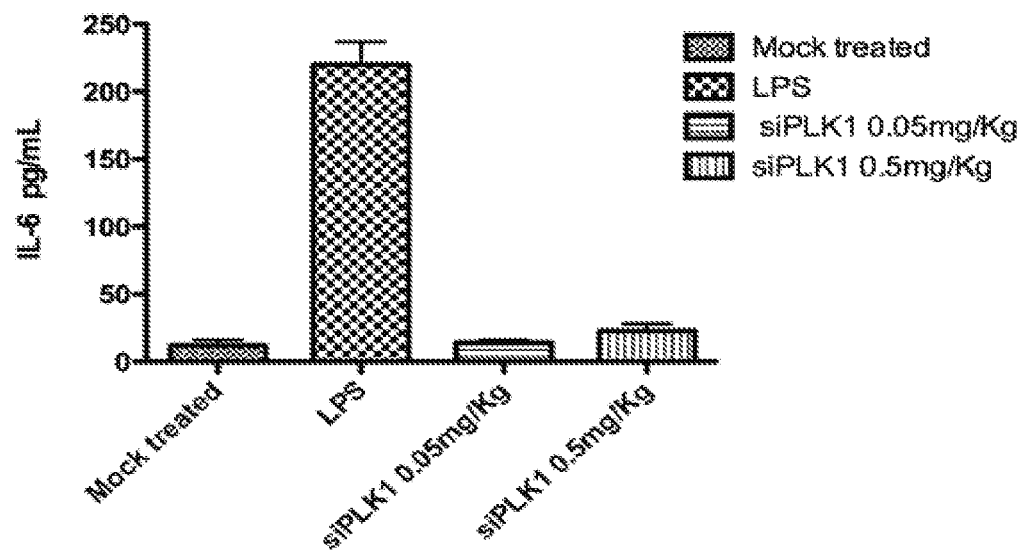

Next, in order to show that siRNA entrapped in the particles does not trigger a proinflammatory response, primary mouse cells were isolated from the brain and the cells were sorted (by FACS) using an anti-mouse CD11b mAb, in order to obtain mouse microglia cells, as these cells may be involved in a potential local inflammatory response when siRNAs are delivered. The cells were incubated with siPLK1 entrapped/encasulated in the particles (HA-LP) at two doses (0.05 and 0.5 mg/Kg siRNA) and probed for TNF-α and IL-6 levels 6 hours post incubation with the primary cells. LPS was used as a positive control. As shown in FIGS. 12B-C, no induction of the proinflammatory cytokines (TNF-α and IL-6, respectively) in the low concentration was obseerved, and a very mild induction was detected in the higher concentration. Thus, these results support the finding that the particles comprising HA (HA-LP) protect siRNA in a very efficient manner and do not trigger a proinflammatory response even when directly interacting with CD11b+ cells.

Figure 12D:
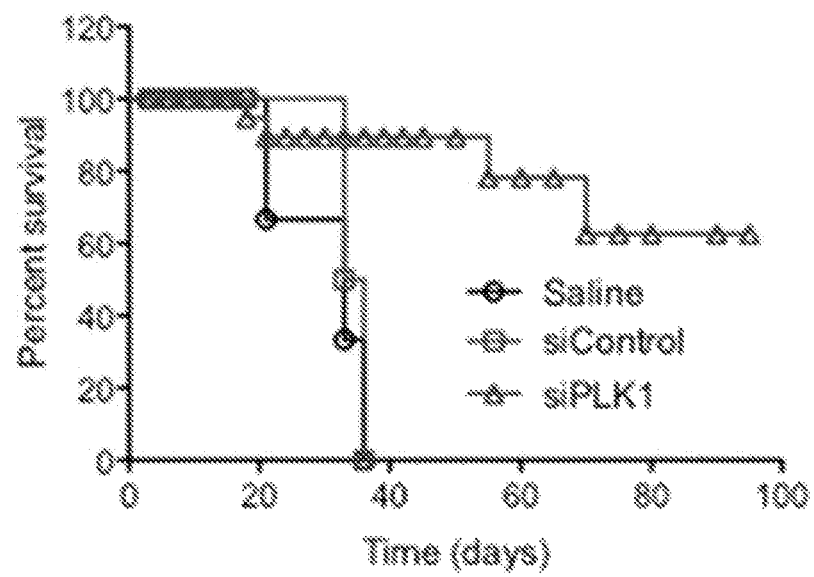

It has been shown that robust silencing of PLK1 induced tumor regression in different tumors implanted in nude or SCID mice (Sakurai et. al. (2014). Thus, the orthotopic GBM model was used to examine the effect of PLK1 silencing on the survival of the mice (FIG. 12D). Into the GBM tumor site, 3 µL (per administration) of 0.5 mg/Kg body of particles encapsulating siPLK1 or siLuci were locally administered at days 7, 9, 20 and 22 post tumor inoculation. The median survival of Mock-treated mice was determined to be 33 days. Mice receiving 4 administrations of HA-LP encapsulating siLuc had a median survival of 34.5 days and those receiving HA-LP encapsulating siPLK1 had prolong survival with a remarkable 60% survival at day 95 post tumor inoculation according to Kaplan-Meier survival analysis (p=0.0012, between siPLK1 and siLuci treated group). This is the longest ever reported survival of mice in this orthotopic GBM model. In addition, this is the first time therapeutic siRNAs are being used in localized treatment to achieve therapeutic benefit in an orthotopic model of GBM.

REFERENCES

Manjunath N. and Dykxhoorn Derek M. (2010). Advances in synthetic siRNA delivery. Discovery Medicine, 9(48): 418-430.

Weinstein S. and Peer D. (2010). RNAi nanomedicines: challenges and opportunities within the immune system. Nanotechnology 21, 21(23), 232001, 1-13.

Peer D (2010). Induction of therapeutic gene silencing in leukocyte-implicated diseases by targeted and stabilized nanoparticles: A mini-review. Journal of Controlled Release 148, 63-68.

Schroeder A1, Levins C G, Cortez C, Langer R, Anderson D G. (2010). Lipid-based nanotherapeutics for siRNA delivery. J Intern Med. 2010 January; 267(1):9-21.

Liu H A, Liu Y L, Ma Z Z, Wang J C, Zhang Q (2011). A Lipid Nanoparticle System Improves siRNA Efficacy in RPE Cells and a Laser-Induced Murine CNV Model. Invest Ophthalmol Vis Sci. 2011 Jul. 1; 52(7):4789-94.

Arpicco S1, De Rosa G, Fattal E. (2013). Lipid-Based Nanovectors for Targeting of CD44-Overexpressing Tumor Cells. J Drug Deliv. 2013; 2013:860780.

Shim G, Kim M G, Park J Y, Oh Y K (2013). Application of cationic liposomes for delivery of nucleic acids. Asian journal of pharmaceutical sciences 8, 72-80.

Shulman, Z.; Alon, R. Chapter 14. Real-Time In Vitro Assays for Studying the Role of Chemokines in Lymphocyte Transendothelial Migration Under Physiologic Flow Conditions. *Methods Enzymol* 2009, 461, 311-332.

Peer D, Park E J, Morishita Y, Carman C V, and Shimaoka M (2008). Systemic leukocyte-directed siRNA delivery revealing cyclin D1 as an anti-Inflammation target. Science. 319, 627-630.

Lee H, Mok H, Lee S, Oh Y K, Park T G (2007). Target-specific intracellular delivery of siRNA using degradable hyaluronic acid nanogels. J Control Release. 2007 Jun. 4; 119(2):245-52.

Choi K Y, Chung H, Min K H, Yoon H Y, Kim K, Park J H, Kwon I C, Jeong S Y (2010). Self-assembled hyaluronic acid nanoparticles for active tumor targeting. Biomaterials, January; 31(1):106-14.

Taetz S, Bochot A, Surace C, Arpicco S, Renoir J M, Schaefer U F, Marsaud V, Kerdine-Roemer S, Lehr C M, Fattal E. (2009). Hyaluronic acid-modified DOTAP/DOPE liposomes for the targeted delivery of anti-telomerase siRNA to CD44-expressing lung cancer cells. Oligonucleotides. 2009 June; 19(2):103-16.

Sakurai, Y.; Hatakeyama, H.; Akita, H.; Harashima, H. (2014) Improvement of Doxorubicin Efficacy Using Liposomal Anti-Polo-Like Kinase 1 siRNA in Human Renal Cell Carcinomas. *Mol Pharm* 2014, 11, 2713-2719.

Cohen, K.; Emmanuel, R.; Kisin-Finfer, E.; Shabat, D.; Peer, D. (2014). Modulation of Drug Resistance in Ovarian Adenocarcinoma using Chemotherapy Entrapped in Hyaluronan-Grafted Nanoparticle Clusters. *ACS Nano* 2014, 8, 2183-2195.

Cohen Z. R., Ramishetti S., Peshes-Yaloz N., Goldsmith M., Wohl A., Zibly Z., Peer, D. (2015). Localized RNAi Therapeutics of Chemo-Resistant Grade IV Glioma using Hyaluronan-Grafted Lipid-Based Nanoparticles. ACS Nano 2015, 9 (2), 1581-1591.

What is claimed is:

1. A liposome for delivery of a nucleic acid comprising a lipid membrane encapsulating the nucleic acid, wherein the lipid membrane is composed of a cationic lipid; a membrane stabilizing lipid; a phospholipid conjugated to a PEG-amine; one or more additional PEG derivatives; and optionally one or more phosphatidylamine, wherein said lipid membrane is coated with hyaluronic acid having a molecular weight in the range of about 600-1000 KDa which is bound to said PEG-amine, and wherein said liposome has a diameter of about 50 nm to about 300 nm.

2. The liposome of claim 1, wherein the cationic lipid is selected from DLinDMA, DLin-MC3-DMA and DLin-KC2-DMA; monocationic lipid N-[1-(2,3-Dioleoyloxy)]-N,N,N-trimethylammonium propane (DOTAP), BCAT O-(2R-1,2-di-O-(1'Z, 9'Z-octadecadienyl)-glycerol)-3-N-(bis-2-aminoethyl)-carbamate, BGSC (Bis-guanidinium-spermidine-cholesterol), BGTC (Bis-guanidinium-tren-cholesterol), CDAN (N' -cholesteryl oxycarbony 1-3,7-diazanonane-1,9-diamine), CHDTAEA (Cholesteryl hemidithiodiglycolyl tris(amino(ethyl)amine), DCAT (O-(1, 2-di-O-(9'Z-octadecanyl)-glycerol)-3-N-(bis-2-amino-ethyl)-carbamate), DC-Chol (3β [N-(N', N'-dimethylamin-oethane)-carbamoyl] cholesterol), DLKD (O,O'-Dilauryl N-lysylaspartate), DMKD (O,O'-Dimyristyl N-lysylaspartate), DOG (Diolcylglycerol, DOGS (Dioctadecylamidogly-cylspermine), DOGSDSO (1,2-Dioleoyl-sn-glycero-3-suc-cinyl-2-hydroxyethyl disulfide ornithine), DOPC (1,2-Dioleoyl-sn-glycero-3-phosphocholine), DOPE (1,2-Dioleoyl-sn-glycerol-3-phosphoethanolamine, DOSN (Dioleyl succinyl ethylthioneomycin), DOSP (Dioleyl suc-cinyl paromomycin), DOST (Dioleyl succinyl tobramycin), DOTAP (1,2-Uiolcoyl-3-trimethyl ammoniopropane), DOTMA (N'[1-(2,3-Dioleyloxy)propyl]-N,N,N-trimethv-lammonium chloride), DPPES (Di-palmitoyl phosphatidyl ethanolamidosperminc), DDAB, and DODAP.

3. The liposome of claim 1, wherein the membrane stabilizing lipid is selected from the group consisting of cholesterol, phospholipids, cephalins, sphingolipids, and glycoglycerolipids.

4. The liposome of claim 1, wherein the phospholipid conjugated to a PEG-amine bound to hyaluronic acid constitutes about 0.25 mole% to 3 mole% of the lipid membrane.

5. The liposome of claim 1 containing one or more phosphatidylamine selected from 1,2-dilauroyl-L-phospha-tidyl-ethanolamine (DLPE), 1,2-Dioleoyl-sn-glycero-3-phosphoethanolamine (DOPE) 1,2-Diphytanoyl-sn-glycero-3-phosphoethanolamine (DPhPE) 1,3-Dipalmitoyl-sn-glycero-2-phosphoethanolamine (1,3-DPPE) 1-Palmitoyl-3-oleoyl-sn-glycero-2-phosphoethanolamine (1,3-POPE), Biotin-Phosphatidylethanolamine, 1,2-Dimyristoyl-sn-glycero-3-phosphoethanolamine(DMPE), 1,2-Distearoyl-sn-glycero-3-phosphoethanolamine (DSPE), and Dipalmi-toylphosphatidyletthanolamine (DPPE).

6. The liposome of claim 1, wherein the additional PEG derivative is selected from DMG-PEG, PEG-cDMA, 3-N-(-methoxy poly(ethylene glycol)2000)carbamoyl-1,2-dimyristyloxy-propylamine; PEG-cDSA, 3-N-(-methoxy poly(ethylene glycol)2000)carbamoyl-1,2-distearyloxy-pro-pylamine, and combinations thereof.

7. The liposome of claim 1, wherein the nucleic acid is selected from DNA, RNA, and modified forms thereof.

8. The liposome of claim 7, wherein the RNA is selected from siRNA, miRNA, shRNA, antisense RNA, mRNA, modified mRNA, and combinations thereof.

9. A composition comprising a plurality of liposomes according to claim 1, wherein the liposomes are capable of delivering the nucleic acid to a target site, wherein the target site is selected from a cell, a tissue, an organ, and a microorganism.

10. The composition of claim 9, wherein the target cell harbors a CD44 receptor.

11. The composition of claim 9 in a dosage form suitable for localized administration or for administration via a route selected from oral, parenteral and topical.

12. A method for treating cancer, comprising the step of administering to a subject in need thereof a composition according to claim 11.

13. The method of claim 12, wherein the cancer is selected from Adenocarcinoma, and Glioblastoma Multi-forme (GBM).

14. A method for the preparation of the liposome of claim 1, the method comprising the steps of:
   a) forming a lipid phase comprising the step of mixing a cationic lipid, a membrane stabilizing lipid, a phospholipid conjugated to a PEG-amine, one or more additional PEG derivatives, and optionally one or more phosphatidylamine, in an organic solvent at a desired ratio and forming a lipid mixture,
   b) generating the liposome by the step of: introducing a nucleic acid in an aqueous solution into the lipid mixture of step (a); and
   c) adding an activated hyaluronic acid to the mixture.

15. The method of claim 14, wherein the hyaluronic acid is activated by dissolving a hyaluronic acid in an acidic buffer and adding a crosslinker to form an activated hyaluronic acid.

16. A method for the preparation of the liposome of claim 1, the method comprising the steps of:
   a) forming a lipid phase comprising the steps of:
      i) mixing a cationic lipid, a membrane stabilizing lipid, a phospholipid conjugated to a PEG-amine, one or more additional PEG derivatives, and optionally one or more phosphatidylamine, in an organic solvent at a desired ratio and forming a lipid mixture,
ii) suspending the lipid mixture in a buffer to generate multilamellar vesicles;
b) generating the liposome by the steps of:
i) incubating the lipid phase of step (a) with the nucleic acid; and
ii) adding an activated hyaluronic acid to the mixture.

17. A liposome for delivery of a nucleic acid comprising a lipid membrane encapsulating the nucleic acid, wherein the lipid membrane is composed of a plurality of lipids comprising a cationic lipid, a membrane stabilizing lipid, a phospholipid conjugated to a PEG-amine, optionally one or more additional PEG derivatives and optionally one or more phosphatidylamine; wherein the external surface of said lipid membrane is coated with hyaluronic acid covalently attached to said PEG-amine; wherein the hyaluronic acid has a molecular weight in the range of about 600-1000 KDa; and wherein said liposome has a diameter of about 50 nm to about 300 nm.

18. The liposome of claim 17, wherein the cationic lipid is selected from: DLinDMA, DLin-MC3-DMA and DLin-KC2-DMA; monocationic lipid N-[1-(2,3-Dioleoyloxy)]-N,N,N-trimethylammonium propane (DOTAP), BCAT O-(2R-1,2-di-O-('Z, 9'Z-octadecadienyl)-glycerol)-3-N-(bis-2-aminoethyl)-carbamate, BGSC (Bis-guanidinium-spermidine-cholesterol), BGTC (Bis-guanidinium-tren-cholesterol), CDAN (N' -cholesteryl oxycarbony 1-3,7-diazanonane-1,9-diamine), CHDTAEA (Cholesteryl hemidithiodiglycolyl tris(amino(ethyl)amine), DCAT (O-(1,2-di-O-(9'Z-octadecanyl)-glycerol)-3-N-(bis-2-amino-ethyl)-carbamate), DC-Chol (3β [N-(N', N'-dimethylaminoethane)-carbamoyl] cholesterol), DLKD (O,O'-Dilauryl N-lysylaspartate), DMKD (O,O'-Dimyristyl N -lysylaspartate), DOG (Diolcylglycerol, DOGS (Dioctadecylamidogly-cylspermine), DOGSDSO (1,2-Dioleoyl-sn-glycero-3-succinyl-2-hydroxyethyl disulfide ornithine), DOPC (1,2-Dioleoyl-sn-glycero-3-phosphocholine), DOPE (1,2-Dioleoyl-sn-glycerol -3-phosphoethanolamine, DOSN (Dioleyl succinyl ethylthioneomycin), DOSP (Dioleyl succinyl paromomycin), DOST (Dioleyl succinyl tobramycin), DOTAP (1,2-Uiolcoyl-3-trimethyl ammoniopropane), DOTMA (N'[1-(2,3-Dioleyloxy)propyl]-N,N,N-trimethylammonium chloride), DPPES (Di-palmitoyl phosphatidyl ethanolamidosperminc), DDAB, and DODAP.

19. The liposome of claim 17, wherein the membrane stabilizing lipid is selected from the group consisting of cholesterol, phospholipids, cephalins, sphingolipids, and glycoglycerolipids.

20. The liposome of claim 17, wherein the phospholipid conjugated to a PEG-amine bound to hyaluronic acid constitutes about 0.25 mole % to 3 mole % of the lipid membrane.

21. The liposome of claim 17, containing one or more phosphatidylamine selected from: 1,2-dilauroyl-L-phosphatidyl-ethanolamine (DLPE), 1,2-Dioleoyl-sn-glycero-3-phosphoethanolamine (DOPE) 1,2-Diphytanoyl-sn-glycero-3-phosphoethanolamine (DPhPE) 1,3-Dipalmitoyl-sn-glycero-2-phosphoethanolamine (1,3-DPPE) 1-Palmitoyl-3-oleoyl-sn-glycero-2-phosphoethanolamine (1,3-POPE), Biotin-Phosphatidylethanolamine, 1,2-Dimyristoyl-sn-glycero-3-phosphoethanolamine(DMPE), 1,2-Distearoyl-sn-glycero-3-phosphoethanolamine (DSPE), and Dipalmitoylphosphatidylethanolamine (DPPE).

22. The liposome of claim 17, containing one or more additional PEG derivatives selected from: DMG-PEG, PEG-cDMA, 3-N-(-methoxy poly(ethylene glycol)2000)carbamoyl-1,2-dimyristyloxy-propylamine; PEG-cDSA, 3-N-(-methoxy poly(ethylene glycol)2000)carbamoyl-1,2-distearyloxy-propylamine, and combinations thereof.

23. The liposome of claim 17, wherein the nucleic acid is selected from DNA, RNA and modified forms thereof, wherein the RNA is selected from siRNA, miRNA, shRNA, antisense RNA, mRNA, modified mRNA, and combinations thereof.

24. A composition comprising a plurality of liposomes according to claim 17, wherein the liposomes are capable of delivering the nucleic acid to a target site, wherein the target site is selected from a cell, a tissue, an organ, and a microorganism.

25. The composition of claim 24, wherein the target cell harbors a CD44 receptor.

26. The composition of claim 24 in a dosage form suitable for localized administration or administration via a route selected from oral, parenteral and topical.

27. A method for treating cancer, comprising the step of administering to a subject in need thereof a composition according to claim 26.

28. A method for the preparation of the liposome of claim 17, the method comprising the steps of:
a) forming a lipid phase comprising the step of mixing a plurality of lipids comprising a cationic lipid, a membrane stabilizing lipid, a phospholipid conjugated to a PEG-amine; optionally one or more additional PEG derivatives, and optionally one or more phosphatidylamine, in an organic solvent at a desired ratio and forming a lipid mixture,
b) generating the liposome by the step of: introducing a nucleic acid in an aqueous solution into the lipid mixture of step a); and
c) adding an activated hyaluronic acid to the mixture.

29. The method of claim 28, wherein the hyaluronic acid is activated by dissolving a hyaluronic acid in an acidic buffer and adding a crosslinker to form an activated hyaluronic acid.

30. A method for the preparation of the liposome of claim 17, the method comprising the steps of:
a) forming a lipid phase comprising the steps of:
i) mixing a plurality of lipids comprising a cationic lipid, a membrane stabilizing lipid, a phospholipid conjugated to a PEG-amine, optionally one or more additional PEG derivatives, and optionally one or more phosphatidylamine, in an organic solvent at a desired ratio and forming a lipid mixture,
ii) suspending the lipid mixture in a buffer to generate multilamellar vesicles;
b) generating the liposome by the steps of:
i) incubating the lipid phase of step a) with the nucleic acid; and
ii) adding an activated hyaluronic acid to the mixture.

* * * * *

SEQUENCE LISTING

```
<160> NUMBER OF SEQ ID NOS: 8

<210> SEQ ID NO 1
<211> LENGTH: 21
<212> TYPE: RNA
<213> ORGANISM: Artificial sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: 2'-O-methylation
<220> FEATURE:
<221> NAME/KEY: modified_base
<222> LOCATION: (2)..(2)
<223> OTHER INFORMATION: 2'-O-methylation
<220> FEATURE:
<221> NAME/KEY: modified_base
<222> LOCATION: (11)..(11)
<223> OTHER INFORMATION: 2'-O-methylation
<220> FEATURE:
<221> NAME/KEY: modified_base
<222> LOCATION: (12)..(12)
<223> OTHER INFORMATION: 2'-O-methylation
<220> FEATURE:
<221> NAME/KEY: modified_base
<222> LOCATION: (14)..(14)
<223> OTHER INFORMATION: 2'-O-methylation
<220> FEATURE:
<221> NAME/KEY: modified_base
<222> LOCATION: (20)..(20)
<223> OTHER INFORMATION: 2'-O-methylation

<400> SEQUENCE: 1
ugaagaagau cacccuccuu a                                              21

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
accagcacgt cgtaggattc                                                20

<210> SEQ ID NO 3
<211> LENGTH: 19
<212> TYPE: DNA
<213> ORGANISM: Artificial sequence
<220> FEATURE:
<223> OTHER INFORMATION: Primer

<400> SEQUENCE: 3
caagcacaat tgccgtagg                                                 19

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
tcagggtttc acatttggca                                                20

<210> SEQ ID NO 5
<211> LENGTH: 21
<212> TYPE: DNA
<213> ORGANISM: Artificial sequence
```

```
<220> FEATURE:
<223> OTHER INFORMATION: siRNA

<400> SEQUENCE: 5
guaggacucu cauucgggat t                                              21

<210> SEQ ID NO 6
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (5)..(5)
<223> OTHER INFORMATION: 2'-O-Me
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (12)..(12)
<223> OTHER INFORMATION: 2'-O-Me
<220> FEATURE:
<221> NAME/KEY: modified_base
<222> LOCATION: (14)..(17)
<223> OTHER INFORMATION: 2'-O-Me
<220> FEATURE:
<221> NAME/KEY: modified_base
<222> LOCATION: (20)..(21)
<223> OTHER INFORMATION: phosphorothioate linkage
<220> FEATURE:
<221> NAME/KEY: modified_base
<222> LOCATION: (20)..(21)
<223> OTHER INFORMATION: Deoxyribonucleotide

<400> SEQUENCE: 6
cuuacgcuga guacuucgat t                                              21

<210> SEQ ID NO 7
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: modified_base
<222> LOCATION: (7)..(7)
<223> OTHER INFORMATION: 2'-OMe
<220> FEATURE:
<221> NAME/KEY: modified_base
<222> LOCATION: (11)..(11)
<223> OTHER INFORMATION: 2'-OMe
<220> FEATURE:
<221> NAME/KEY: modified_base
<222> LOCATION: (16)..(16)
<223> OTHER INFORMATION: 2'-OMe
<220> FEATURE:
<221> NAME/KEY: modified_base
<222> LOCATION: (20)..(21)
<223> OTHER INFORMATION: phosphorothioate linkage
<220> FEATURE:
<221> NAME/KEY: modified_base
<222> LOCATION: (20)..(21)
<223> OTHER INFORMATION: Deoxyribonucleotide

<400> SEQUENCE: 7
ucgaaguacu cagcguaagt t                                              21
```

```
<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
gagcatggat cggaaaacca                                              20
```